US009198731B2

(12) United States Patent
Balaji et al.

(10) Patent No.: US 9,198,731 B2
(45) Date of Patent: Dec. 1, 2015

(54) INTEGRATED SURGICAL CUTTING SYSTEM

(71) Applicant: University of Utah Research Foundation, Salt Lake City, UT (US)

(72) Inventors: Alagar K. Balaji, Salt Lake City, UT (US); William T. Couldwell, Salt Lake City, UT (US); Charles L. Thomas, Salt Lake City, UT (US); Joel D. MacDonald, Salt Lake City, UT (US); Bradley C. Hansen, La Jolla, CA (US); Aniruddha LaPalikar, Nagpur (IN); Bharat Thakkar, Santa Clara, CA (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/626,009

(22) Filed: Feb. 19, 2015

(65) Prior Publication Data
US 2015/0157413 A1   Jun. 11, 2015

Related U.S. Application Data

(62) Division of application No. 12/740,281, filed as application No. PCT/US2008/082298 on Nov. 3, 2008, now Pat. No. 8,965,485.

(60) Provisional application No. 60/984,670, filed on Nov. 1, 2007.

(51) Int. Cl.
*A61B 5/05* (2006.01)
*A61B 19/00* (2006.01)
*A61B 17/32* (2006.01)
*G05B 19/402* (2006.01)
*A61B 18/20* (2006.01)

(52) U.S. Cl.
CPC .............. *A61B 19/2203* (2013.01); *A61B 17/32* (2013.01); *A61B 18/20* (2013.01); *A61B 19/46* (2013.01); *A61B 19/50* (2013.01); *A61B 19/52* (2013.01); *A61B 19/5225* (2013.01); *G05B 19/402* (2013.01); *A61B 19/56* (2013.01); *A61B 2019/2207* (2013.01); *A61B 2019/461* (2013.01); *A61B 2019/507* (2013.01); *A61B 2019/524* (2013.01); *A61B 2019/5236* (2013.01); *A61B 2019/5238* (2013.01); *A61B 2019/5276* (2013.01); *G05B 2219/45169* (2013.01); *G05B 2219/45171* (2013.01)

(58) Field of Classification Search
CPC .......... A61B 5/05; A61B 19/50; A61B 19/52; A61B 17/32; G05B 19/402
USPC ............. 600/410, 414, 424, 429; 606/96, 130
See application file for complete search history.

(56) References Cited

U.S. PATENT DOCUMENTS 6,684,098 B2 * 1/2004 Oshio et al. ................... 600/429
7,815,644 B2 * 10/2010 Masini ........................ 606/86 R

* cited by examiner

*Primary Examiner* — Victor Nguyen
(74) *Attorney, Agent, or Firm* — Ballard Spahr LLP

(57) ABSTRACT

Integrated surgical systems and methods for using same are provided that can receive scanned images and produce a three dimensional model from the images. Based at least in part on the three dimensional model, a processor generates code defining an optimized tool path, which is sent to a surgical machining system that can machine the desired portion of the patient. In one exemplary aspect, the integrated system operates in a clearly defined and pre-programmed manner with no necessity for in-situ sensory or guidance feedback.

14 Claims, 22 Drawing Sheets

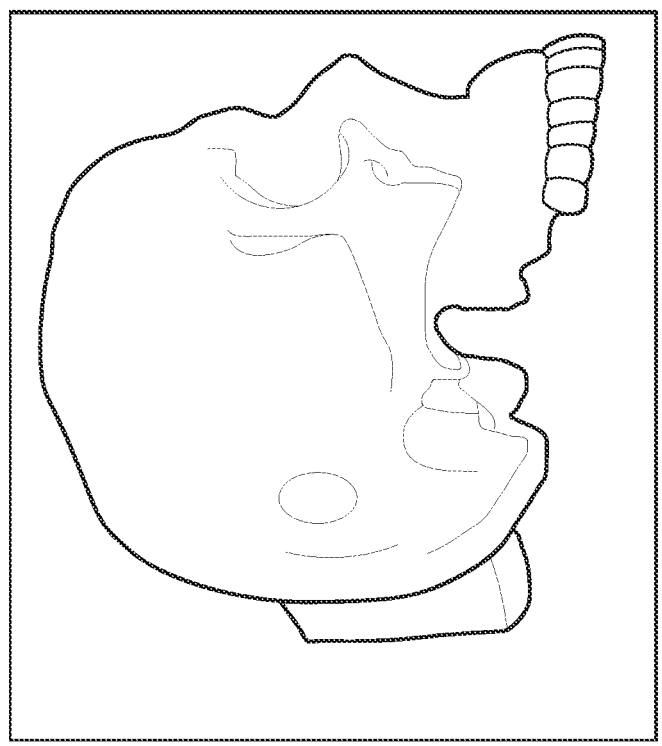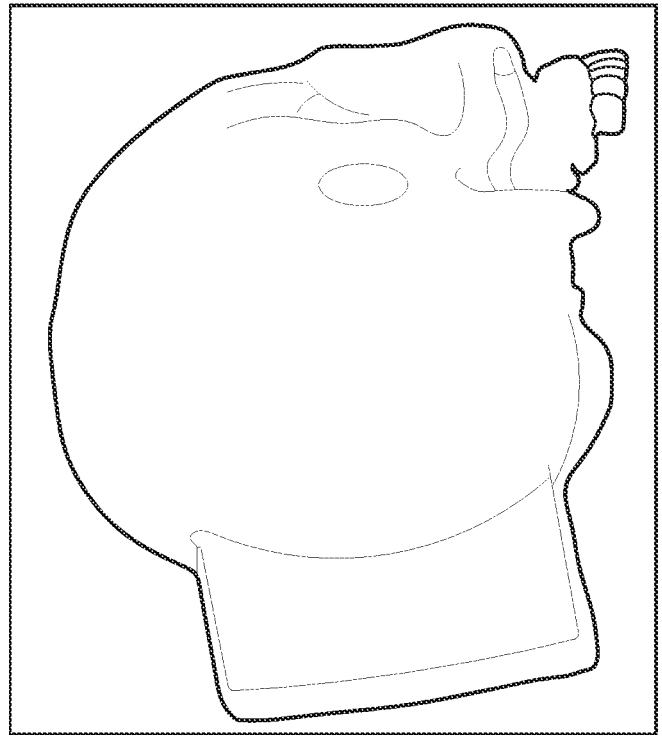
FIG. 19

INTEGRATED SURGICAL CUTTING SYSTEM

CROSS-REFERENCE TO RELATED APPLICATIONS

This application is a divisional of co-pending U.S. patent application Ser. No. 12/740,281, filed Apr. 28, 2010, which is a §371 national phase filing of International Patent Application No. PCT/US2008/082298, filed Nov. 3, 2008, which claims priority to and the benefit of the filing date of U.S. Provisional Patent Application No. 60/984,670, filed Nov. 1, 2007, which applications are incorporated herein by reference in their entirety.

FIELD

This invention relates generally to computer controlled systems for use in surgical applications involving machining of bone, other tissue, and/or other anatomical structures and methods for using same. More specifically, aspects of the invention relate to a robust, yet simple computer numerical controlled (CNC) surgical cutting system interfaced with three dimensional medical image data.

BACKGROUND

Automation in the field of surgical treatments has been a growing field in the past decade. Medical robots are being developed to assist with some surgeries, however, known robot systems are extremely expensive and generally cost upwards of $750,000.

Despite the advances in medical robotics, many surgical procedures continue to be performed manually by surgeons and are therefore more time consuming, which is both more expensive, and more susceptible to human error. For example, certain neurosurgeries require a surgeon to access the brain through the temporal bone. Machining an adequate opening through the temporal bone is currently performed manually. Due to the criticality of brain and brain tumor surgeries, it will be appreciated that even a minor mistake on the part of the surgeon can result in severe consequences. The surgical procedure generally entails a craniotomy (removal of bone flap) and machining through the temporal bone. In one example, a channel or hole is created in the temporal bone to access the brain. Surgeons often use pneumatic hand drills at very high rotational speeds to perform the surgery. The surgeon must rely on the information he has from any preoperative images that were taken (such as CT scans) to perform the machining. Thus, the process is highly susceptible to human error.

Furthermore, such temporal bone procedures usually take a long time (three to four hours) to simply drill the hole in the temporal bone. The expense of the surgeon performing the machining for several hours adds to the already high cost of these surgeries. Additionally, having the lesion open for such long time periods makes the patient susceptible to infections that may further complicate health issues.

Thus, there is a need in the art for automated systems and methods for assisting in neurological surgeries and other surgeries that involve machining through bone, tissue, and/or other desired anatomical structures that reduce the overall duration of the surgeries, minimize human error, and minimize overall cost of the surgeries.

SUMMARY

In accordance with the purpose(s) of this invention, as embodied and broadly described herein, this invention, in one aspect, relates to integrated surgical systems and methods for using same. In one aspect, the integrated surgical system comprises a scanning or imaging device for scanning and/or imaging a targeted portion of a patient, such as, for example and without limitation, a patient's skull for the production of two-dimensional (2D) images of the targeted portion. The 2D images are transmitted to a processor that is configured to generate a three-dimensional (3D) model from the received 2D images. In another aspect, a physician or surgeon can use the integrated system software to define a location on the targeted portion of the patient to be machined and can define the parameters of the machined hole, feature(s) or surface(s) (such as the axis, radius, and depth). The processor generates code that defines an optimized tool path based on the surgeon's input. In a further aspect, the optimized tool path can be sent to a surgical machining system that is configured to machine the hole into the targeted portion of the patient. In yet another aspect, the surgical machining system is configured to allow the machining tool of the surgical machining system to operate within a simple, yet robust five-degree of freedom operating environment, which allows the hole or finished surface to be machined at any angle and any position as defined by the surgeon.

In one aspect, the integrated surgical system can comprise a surgical machining system and an imaging device for producing two-dimensional medical image data. In another aspect, the integrated surgical system can then translate this two-dimensional medical image data into a three-dimensional medical model that can then be programmed for surgery by a surgical specialist or other user using an interactive graphical user interface (GUI). In operation, in yet another aspect, the surgical specialist or other user registers the patient with respect to the integrated system, such that the surgical CNC machining system can then machine a hole as directed by the surgical specialist or other user via inputs into the system. In a further aspect, it is contemplated that the surgical machining system can be interfaced with an interactive software that controls the surgical cutting system.

In one aspect, the surgical machining system can comprise a contact cutting tool such as, for example and without limitation, a bio-compatible end-mill, and the like. In another aspect, the surgical machining system can comprise a non-contact tool such as a laser. Of course it is contemplated that the surgical machining system can be operably coupled to any desired surgical tool for subsequent operation along the generated optimized machine tool path.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention.

FIG. 19 shows a model of a skull having a hole machined therein by exemplary systems of the present invention.

DETAILED DESCRIPTION

Figure 1A:
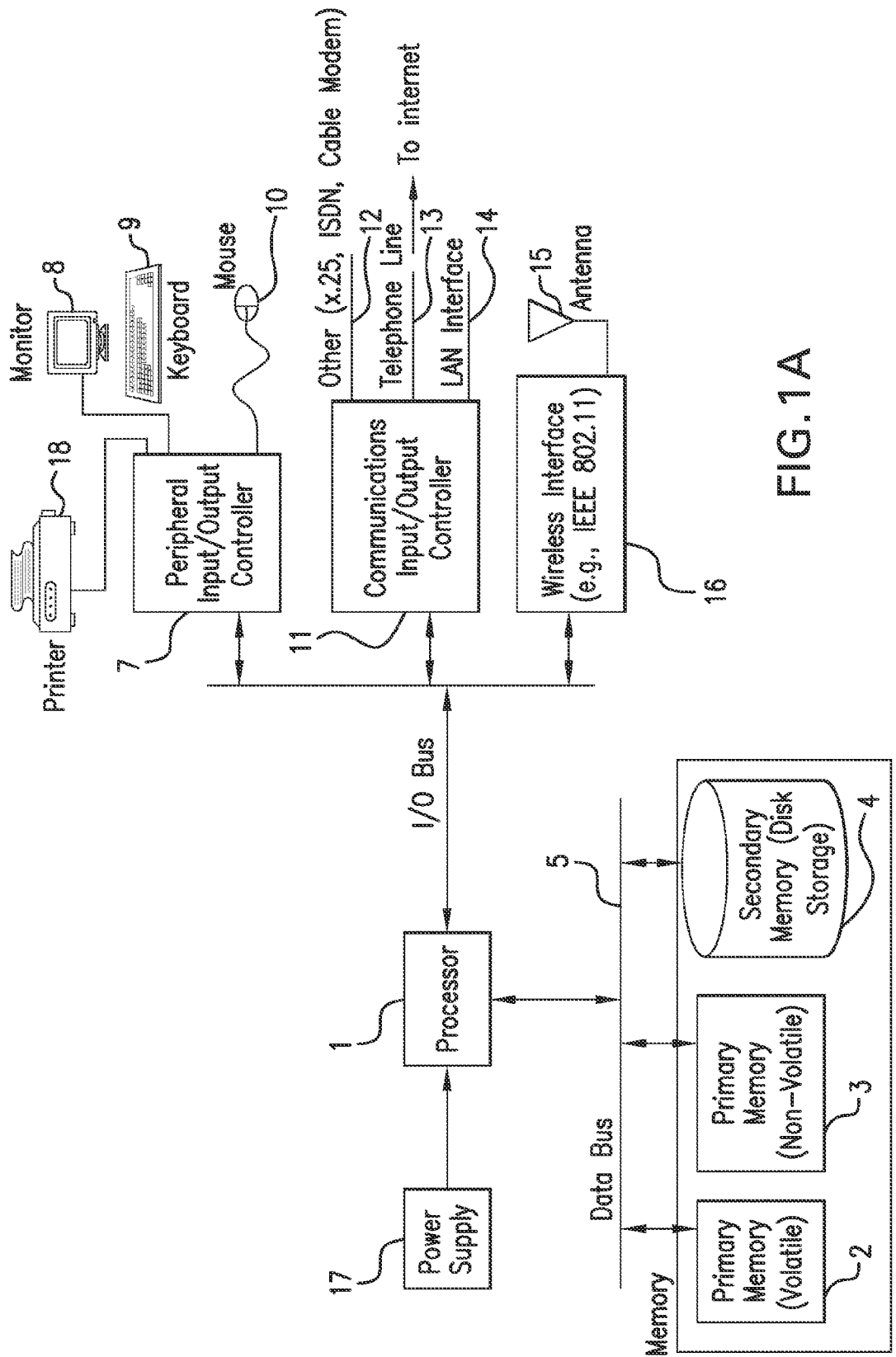
FIG. 1A illustrates an exemplary computing device, according to one aspect of the present invention.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "machining tool" can include two or more such machining tools unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant bath in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to the present preferred aspect(s) of the invention, examples of which are illustrated in the accompanying drawings. Wherever possible, the same reference numbers are used throughout the drawings to refer to the same or like parts.

As used herein, the term "region" with respect to a patient, may include, but is not limited to including, any general and/or specific portion of the patient, whether such portion be a single point on the patient or a general area of the patient that includes a plurality of single points. As used herein, the terms "property" and "properties" may include, but are not limited to including, any physical or structural properties of the patient and/or a region(s) thereof such as, but not limited to, a size, a shape, a location, and/or an orientation. Of course, it is contemplated that other properties not described herein may be included within the meaning of the terms "property" and "properties" as used herein.

As may be appreciated by one skilled in the art, aspects of the present invention may be implemented as a method, a system, or a computer program product or any combination thereof. Accordingly, aspects may take the form of an entirely hardware embodiment, an entirely software embodiment, or an embodiment combining software and hardware aspects. Furthermore, implementations of various aspects may take the form of a computer program product on a computer-readable storage medium having computer-readable program instructions (e.g., computer software) embodied in the storage medium. More particularly, implementations of the preferred embodiments may take the form of web-implemented computer software. Any suitable computer-readable storage medium may be utilized including hard disks, CD-ROMs, optical storage devices, or magnetic storage devices.

Various aspects of the present invention are described below with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In the various aspects referenced herein, a "computer" or "computing device" may be referenced. Such computer may be, for example, a mainframe, desktop, notebook or laptop, a hand held device such as a data acquisition and storage device, or other such device. In some instances the computer may be a "dumb" terminal used to access data or processors over a network. Turning to FIG. 1A, one embodiment of a computing device is illustrated that can be used to practice aspects of the preferred embodiment. In FIG. 1A, a processor 1, such as a microprocessor, is used to execute software instructions for carrying out the defined steps. The processor receives power from a power supply 17 that also provides power to the other components as necessary. The processor 1 communicates using a data bus 5 that is typically 16 or 32 bits wide (e.g., in parallel). The data bus 5 is used to convey data and program instructions, typically, between the processor and memory. In the present embodiment, memory can be considered primary memory 2 that is RAM or other forms which retain the contents only during operation, or it may be non-volatile 3, such as ROM, EPROM, EEPROM, FLASH, or other types of memory that retain the memory contents at all times. The memory could also be secondary memory 4, such as disk storage, that stores large amount of data. In some aspects, the disk storage may communicate with the processor using an I/O bus 6 instead or a dedicated bus (not shown).

The secondary memory may be a floppy disk, hard disk, compact disk, DVD, or any other type of mass storage type known to those skilled in the computer arts.

The processor 1 also communicates with various peripherals or external devices using an I/O bus 6. A peripheral I/O controller 7 can be used to provide standard interfaces, such as RS-232, RS422, DIN, USB, or other interfaces as appropriate to interface various input/output devices. Typical input/output devices include local printers 18, a monitor 8, a keyboard 9, and a mouse 10 or other typical pointing devices (e.g., rollerball, trackpad, joystick, etc.).

The processor 1 typically also communicates using a communications I/O controller 11 with external communication networks, and may use a variety of interfaces such as data communication oriented protocols 12 such as X.25, ISDN, DSL, cable modems, etc. The communications controller 11 may also incorporate a modem (not shown) for interfacing and communicating with a standard telephone line 13. Finally, the communications I/O controller may incorporate an Ethernet interface 14 for communicating over a LAN. Any of these interfaces may be used to access a wide area network such as the Internet, intranets, LANs, or other data communication facilities.

Finally, the processor 1 may communicate with a wireless interface 16 that is operatively connected to an antenna 15 for communicating wirelessly with another device, using for example, and not meant be limiting, one of the IEEE 802.11 protocols, 802.15.4 protocol, or a standard 3G wireless telecommunications protocols, such as CDMA2000 1x EV-DO, GPRS, W-CDMA, or other protocol.

Figure 1B:
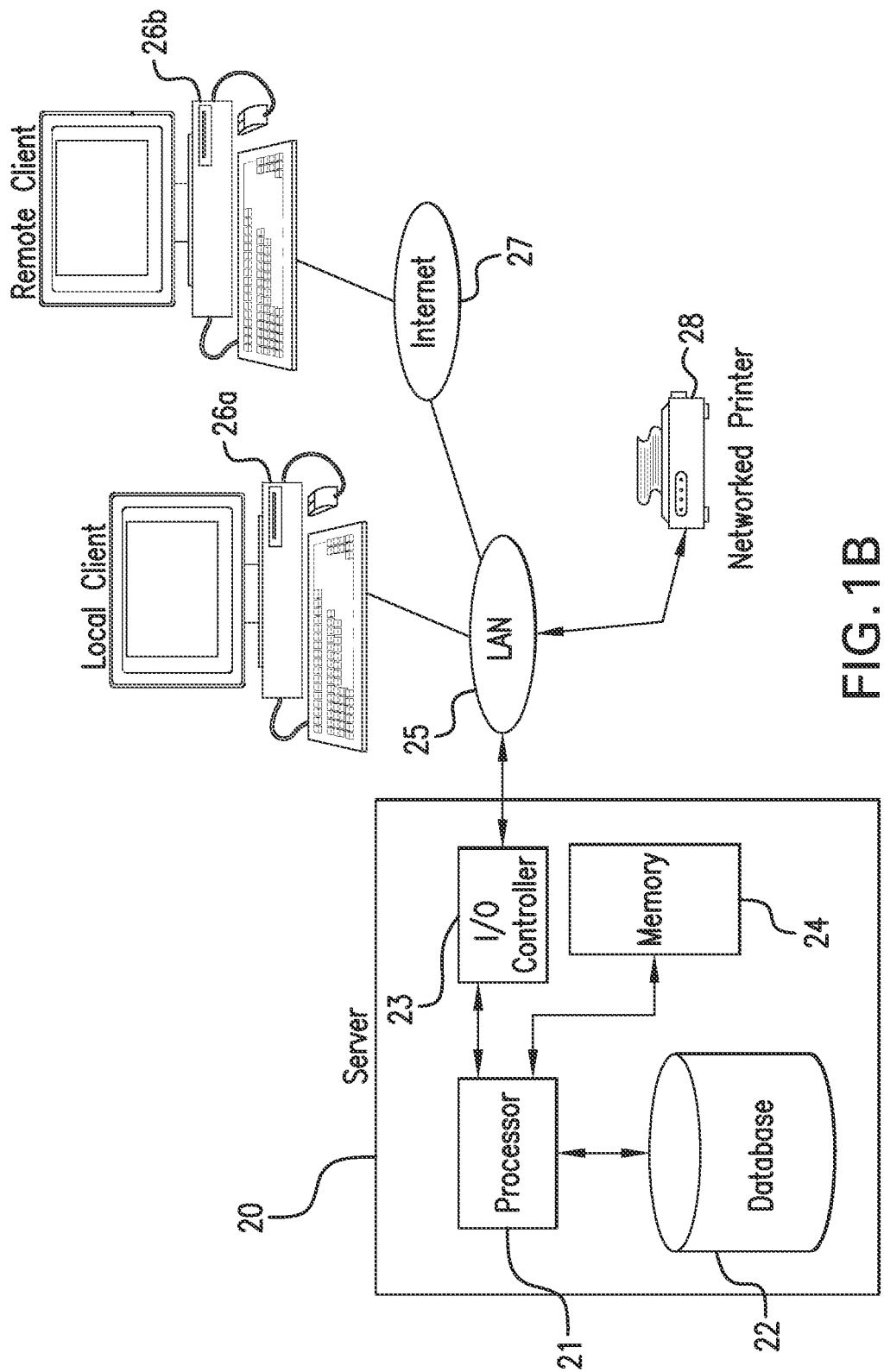
FIG. 1B illustrates an exemplary processing system, according to another aspect of the present invention.

An alternative embodiment of a processing system that may be used is shown in FIG. 1B. In this embodiment, a distributed communication and processing architecture is shown involving a server 20 communicating with either a local client computer 26a or a remote client computer 26b. The server 20 typically comprises a processor 21 that communicates with a database 22, which can be viewed as a form of secondary memory, as well as primary memory 24. The processor also communicates with external devices using an I/O controller 23 that typically interfaces with a LAN 25. The LAN may provide local connectivity to a networked printer 28 and the local client computer 26a. These may be located in the same facility as the server, though not necessarily in the same room. Communication with remote devices typically is accomplished by routing data from the LAN 25 over a communications facility to a wide area network 27, such as the Internet. A remote client computer 26b may execute a web browser, so that the remote client 26b may interact with the server as required by transmitted data, through the wide area network 27, over the LAN 25, and to the server 20.

Those skilled in the art of data networking will realize that many other alternatives and architectures are possible and can be used to practice the preferred embodiments. It is of course contemplated that the exemplary embodiments illustrated in FIGS. 1A and 1B can be modified in different ways and be within the scope of the present invention as claimed.

Figure 2B:
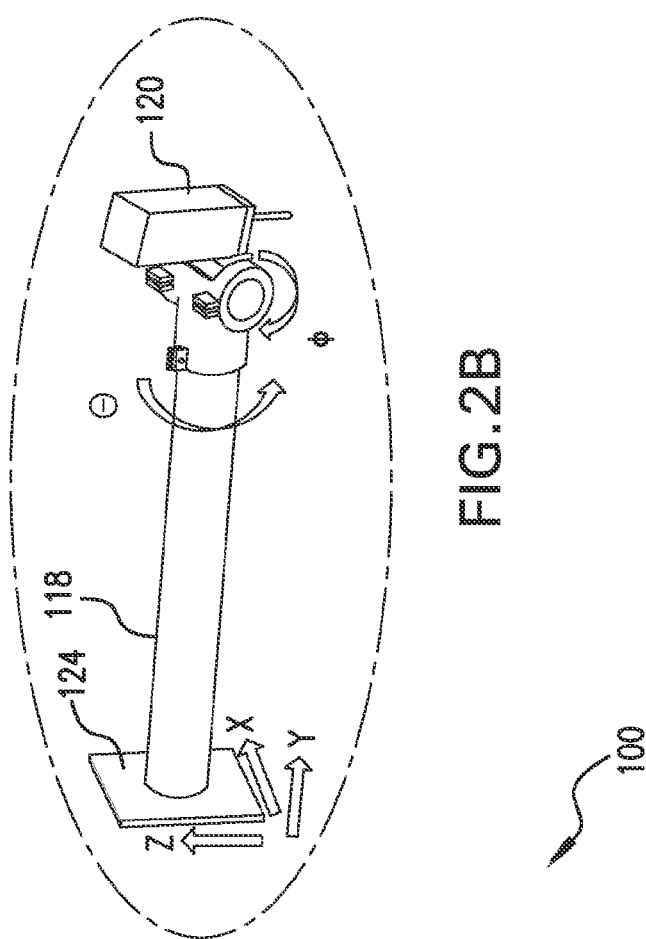
FIG. 2B illustrates the surgical arm and machining tool of FIG. 2A, according to a further aspect of the present invention.
Figure 2A:
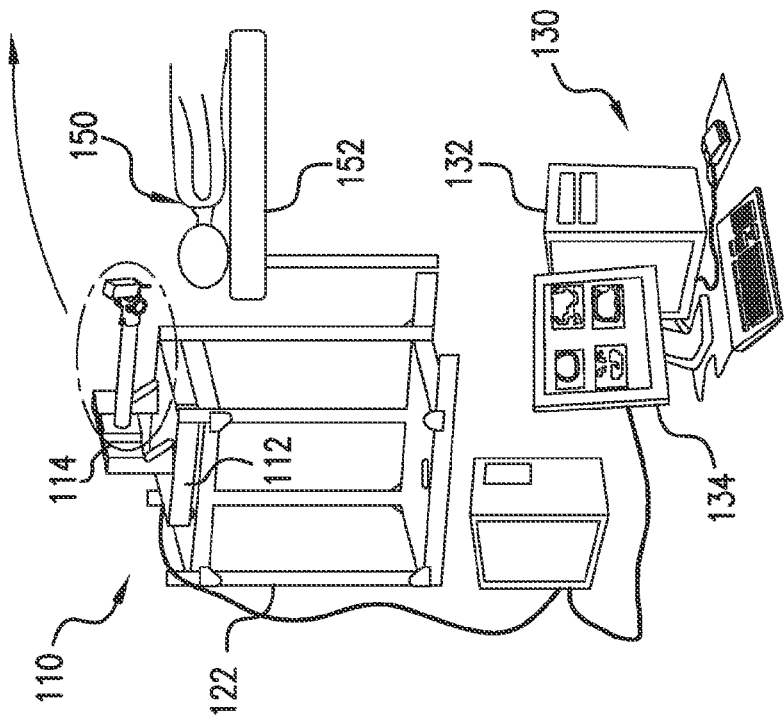
FIG. 2A illustrates an exemplary computer numerical controlled (CNC) system for neurosurgery, according to one aspect of the present invention.

Referring now to FIGS. 2A and 2B, a schematic embodiment of an integrated surgical system 100 is illustrated. In one embodiment, and in optional aspects, it is contemplated that the integrated surgical system 100 can be portable, easily accessible and simple for a surgical specialist or other user to use, and does not depend on continuous visual or other sensory feedback during the procedure (i.e., in one aspect, the surgical path and procedure can be pre-programmed based on the substantially fixed location and geometry of the tissue that needs to be machined). In another aspect, the integrated surgical cutting system can comprise a passive imaging system that allows a surgical specialist or other user to view a 2D and a 3D image of an area on a patient to be operated on and to preplan a desired or optimum machine tool path for reaching the targeted area or portion.

The exemplary integrated surgical system 100 can be configured for machining a desired portion of the patient, such as, but not limited to, substantially spatially fixed tissue and/or non-spatially fixed tissue. As described herein, the integrated surgical system 100 generally includes an imaging device used to image at least one property of the patient and a processor operatively connected to the imaging device for receiving images, such as, for example and not meant to be limiting, 2D images produced by the imaging device of the at least one property of the patient. Generally, and as will be described in more detail below, in one embodiment, the integrated surgical system 100 is operable to determine an actual 3D model of the property of a region of the patient. Moreover, integrated surgical system 100 is also operable to determine a path of a machining tool 120 that is electronically stored in a memory associated with, and operatively connected to, the integrated surgical system.

For example, to assist surgical procedures that fabricate a tooled opening in the selected tissue of the patient, a 3D model of an expected geometry of the component can be generated by the processor. Optionally, the 3D model can comprise the geometry of the surfaces of the desired portion of the patient and/or the finished surfaces that may be machined during the machining process. In one aspect, to fabricate one or more finished surfaces therein the desired portion of the patient, a machine path of the machining tool 120 can be generated based on the generated geometry of the 3D model, and more specifically based on the geometry of the desired finished portion on the patient.

In one aspect, the integrated surgical system 100 can be portable. Due to the portability of the integrated surgical system, it is contemplated that the integrated surgical system 100 can be moved around a hospital effectively without having to resort to large infrastructure changes to the hospital and/or operating rooms in order to accommodate the integrated surgical system.

In one embodiment, it is contemplated that the integrated surgical system 100 can update the path of the machining tool 120 based on actual properties of the regions of the patient being machined, and more specifically based on detected differences between the actual properties of the particular region being machined and the expected properties of the previously generated 3D model.

In one exemplary embodiment, the processor is configured to generate the model of expected geometry of the desired portion of the patient and to generate the desired or optimum machine path of the machining tool 120 based on the geometry of the generated 3D model. In a further aspect, for example, the processor associated with, and operatively connected to, the machining tool 120 controls operation of the machining tool and generates the machine path of the machining tool based on the previously generated 3D geometry of the model. It is contemplated that the memory can be associated with the machining tool 120, for example as apart of the machine including the machining tool. However, it is also contemplated that the memory can be associated with processor and/or the imaging device.

In one exemplary aspect, the desired fabricating path of the machining tool 120 is electronically stored in memory and is executable by the processor. In one embodiment, the machining tool is coupled to a Computer Numerical Control (CNC) machine and the path of the machining tool 120 is a computer numerical control path executed by the processor, which, for example, may control operation of at least a portion of the CNC machine. The processor may be operatively connected to memory for accessing and updating the path of the machining tool 120 stored therein. It should be understood that any number of processors may be used to perform any or all operations of the integrated surgical system 100 generally that are described and/or illustrated herein. Optionally, it is contemplated that, in one embodiment, one or more processor(s) that perform any of the operations described and/or illustrated herein with respect to the illustrated processors may be a part of the surgical machining system that machines the portion of the patient (e.g., a CNC machine), may be a part of a imaging device that images the desired portion of the patient (e.g., the imaging device and associated components thereof), and/or may be a processor dedicated to the integrated surgical system 100 and operatively connected to the surgical machining system and/or the imaging device.

In one aspect, the integrated surgical system 100 is provided that comprises a surgical machining system 110 and a computing device that is configured to at least partially control the surgical machining system. As shown in FIG. 2A, the surgical machining system 110 can comprise a base portion 112 and a support frame 122 configured to position the base portion at a spaced distance from the floor or ground surface in the operating environment. As one will appreciated, it is contemplated that the support frame can be conventionally configured, such as, for example and without limitation, locking wheel castors and the like, to allow for both portability and selective fixation of the surgical machining system relative to the patient.

Figure 3:
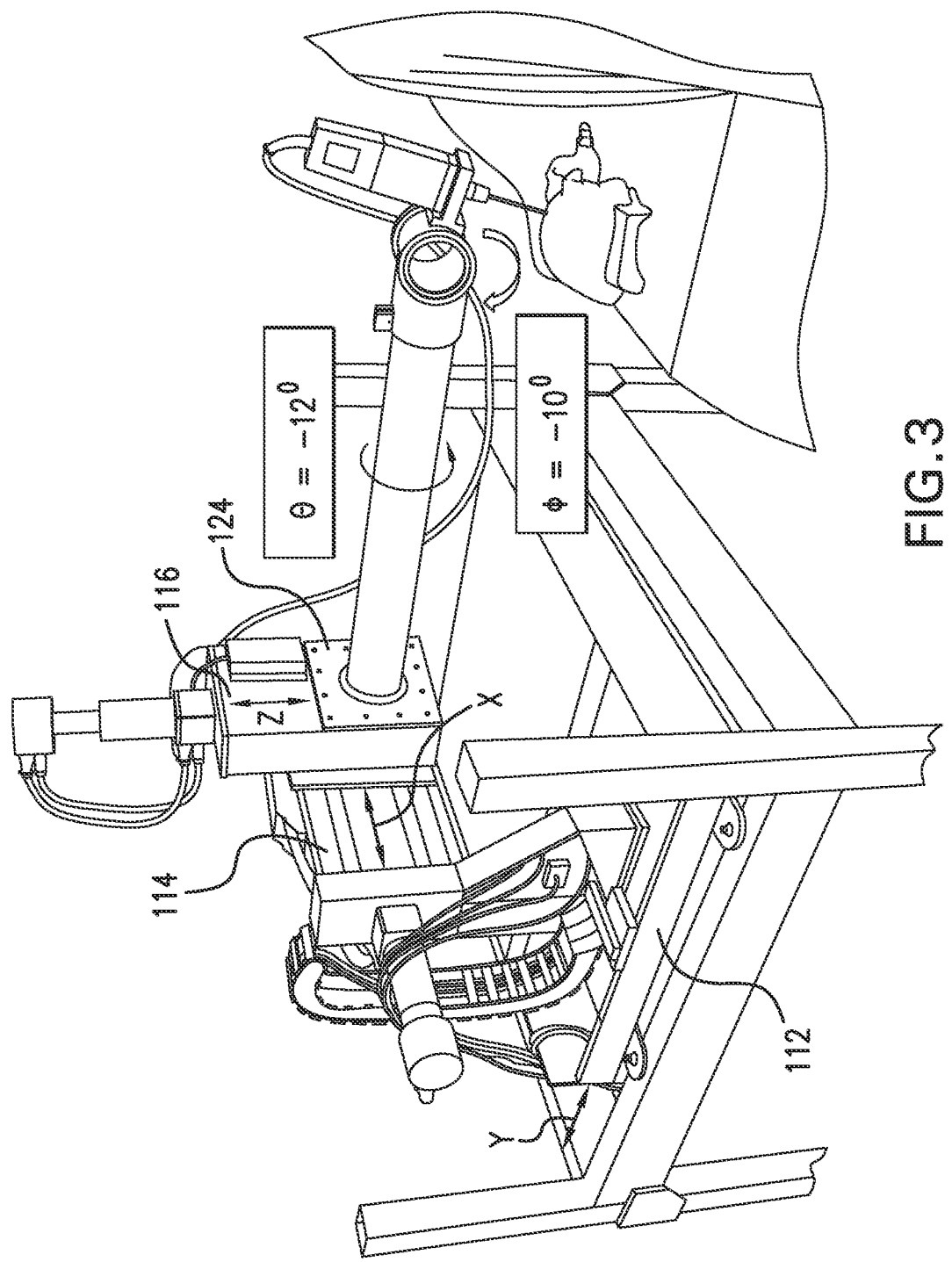
FIG. 3 illustrates an exemplary embodiment of the surgical machining system having a machining tool, according to another aspect of the present invention.

In another aspect, the surgical machining system can further comprise a bridge portion 114 that extends upwardly from the base portion. A surgical arm 118 having a proximal end and an opposed distal end can be attached to the bridge portion at its proximal end. In a further aspect, such as shown in FIG. 3, a mounting member 116 can be mounted on the bridge portion 114 and the surgical arm can extend outwardly from the mounting member. The machining tool 120 can be operably positioned at the distal end of the surgical arm.

As illustrated further in FIG. 3, in one aspect, the base portion can be configured as a three-axis moving gantry system. For example, the entire base portion can move forward and backwards on the support flame 122 along the Y-axis (represented by the arrow "Y"), thereby moving the surgical arm and machining tool closer to or further from the patient 150. The mounting member 116 can move from side to side on the bridge portion 114 along the X-axis (represented by the arrow "X")."). According to a further aspect, the mounting member is configured to also move up and down along the Z-axis (represented by the arrow "Z"). The proximal end of the surgical arm 118 can be welded or otherwise attached to an interfacing plate 124 that is configured to move up and down the mounting member 116 along the Z-axis.

In one aspect, the cooperative three-axis movement of the base portion and the mounting member (in the X, Y, and Z directions) allows the surgical arm to be moved within a three-dimensional space without moving the support frame 122. Additionally, the machining tool 120 can be moved, either under machine control or manually, about two additional axes, $\theta$ and $\Phi$, as shown in FIG. 2B. In another aspect, the machining tool can be moved about the $\theta$ and/or $\Phi$ axes within a range of +/−about 20 degrees. Therefore, it is contemplated that the machining tool can be manipulated and positioned through a five-degree of freedom operating environment, thereby allowing it to access the patient at any desired angle relative to the point of interest on the patient. Additionally, in another aspect, the five-degree of freedom operating environment is capable of achieving advantageous access for the surgical procedure without having to rely on a complex robotic system, which enables the machining tool to be position effectively for performing surgery without unnecessary and/or convoluted positioning of the patient.

Figure 4:
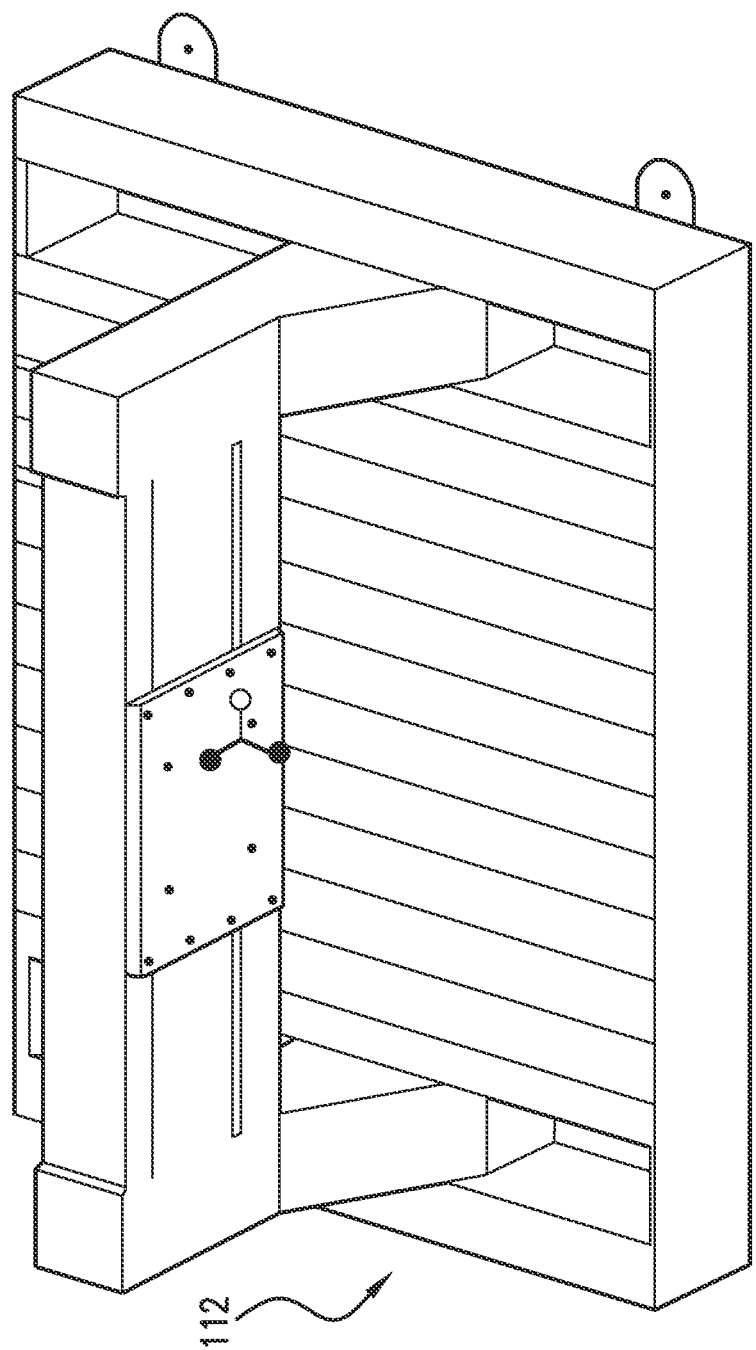
FIG. 4 is a wireframe model of a base portion of a surgical machining system, according to another aspect of the present invention.

FIG. 4 illustrates a wireframe model of one aspect of a base portion 112 of a surgical machining system. In this aspect, the base portion can comprise two opposing troughs that are substantially parallel to the Y-axis. The bridge portion can comprise leg members that are configured to be slideably received within the troughs of the base portion, thereby allowing the bridge portion to move forwards and backwards along the Y-axis, as described above with respect to FIG. 3.

As described above, the surgical arm 118 can extend outwardly from the base portion (i.e., from the bridge portion, the mounting member, and/or the interfacing plate) toward the patient. In a particular aspect, the surgical arm can have a selected length to allow the machining tool to access the patient, while maintaining the rest of the surgical machining system at a desired, predetermined distance from the patient. For example and without limitation, the length can be selected to maintain the machining tool 120 a distance of approximately two feet from the other components of the surgical machining system. Spacing the surgical machining system away from the patient at a desired distance enables the surgical machining system 110 to be used without the need to repeatedly sterilize the entire surgical machining system. For example, it is contemplated that the surgical arm and machining tool can be configured to be removably attached to the surgical machining system, which allows the surgical arm and machining tool to be sterilized prior to surgery without the need to sterilize the entire surgical machining system. Additionally, the offset design of the surgical arm 118 (i.e., the machining tool 120 can be offset from the bridge portion 114, the base portion 112 and the support frame 122 by a predetermined distance) can increase accessibility of the machining site to surgical specialists and/or other operating room personnel.

As shown in FIG. 2B, in one aspect, the surgical arm can have a substantially cylindrical cross-section. Optionally, the surgical arm can have a rectangular, square, or other cross-sectional shape. According to other aspects, the surgical arm can be hollow or solid. In a particular aspect, the surgical arm can be sized and shaped to achieve a desired stiffness and weight to withstand forces and vibrations during machining. Such an arm can be, for example and without limitation, a hollow cylindrical surgical arm such as shown in FIG. 2B. In a further aspect, the surgical arm can substantially comprise aluminum (such as, but not limited to, Al 6061). In yet another aspect and without limitation, the hollow cylindrical surgical arm can be approximately 3.5 inches in diameter, and can have a wall thickness of approximately 0.25 inches, though other diameters and wall thicknesses are also contemplated, as will be described more fully below.

Figure 5:
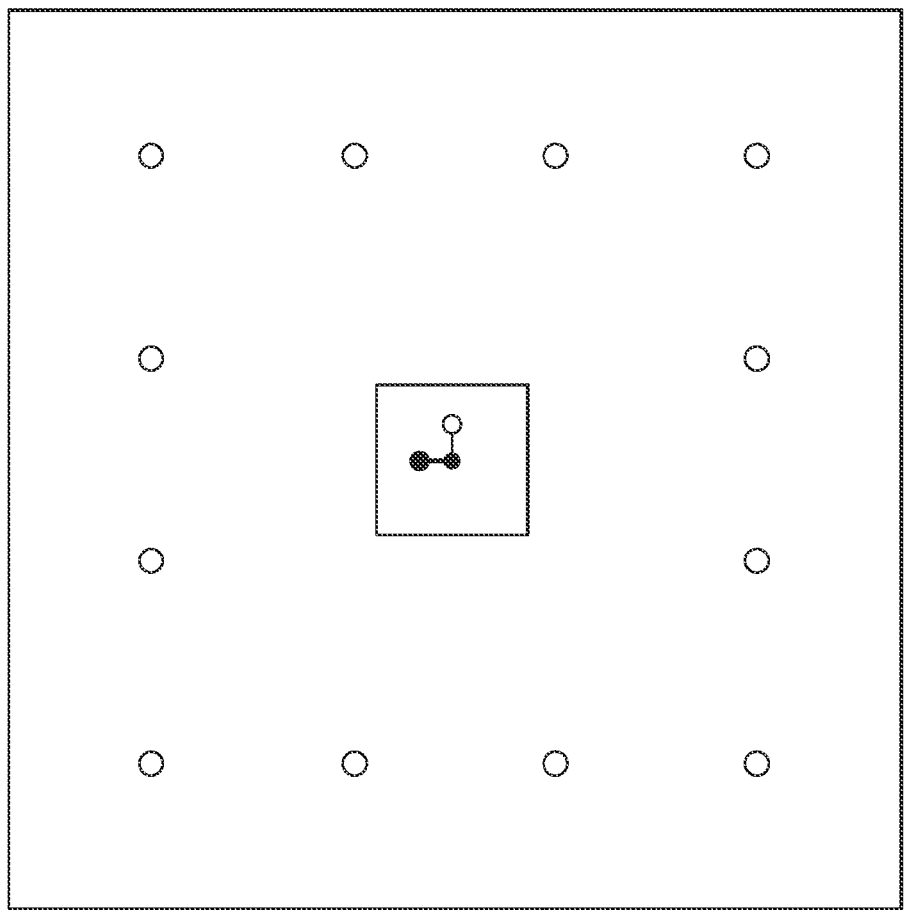
FIG. 5 illustrates an interfacing plate of a surgical machining system, according to one aspect of the present invention.

In yet another aspect, an interfacing plate 124 can be provided to which the proximal end of the surgical arm can be affixed. As illustrated in FIG. 5, the interfacing plate 124 can be substantially rectangular and planar, although other geometric shapes are contemplated. In one aspect, a series of holes are defined in the plate. In a exemplary aspect, twelve holes can be formed, which, in one non-limiting example, can be positioned in an array that is substantially parallel the periphery of the interfacing plate, such as shown in FIG. 5. In one exemplary non-limiting aspect, the holes can be approximately 6 mm in diameter and can be spaced from each other (at their centers) by a distance of approximately 50 mm. In a further aspect, at least one of the holes can be configured to receive a fastener that mounts the interfacing plate to a mounting member (as exemplarily described below).

Figure 6:
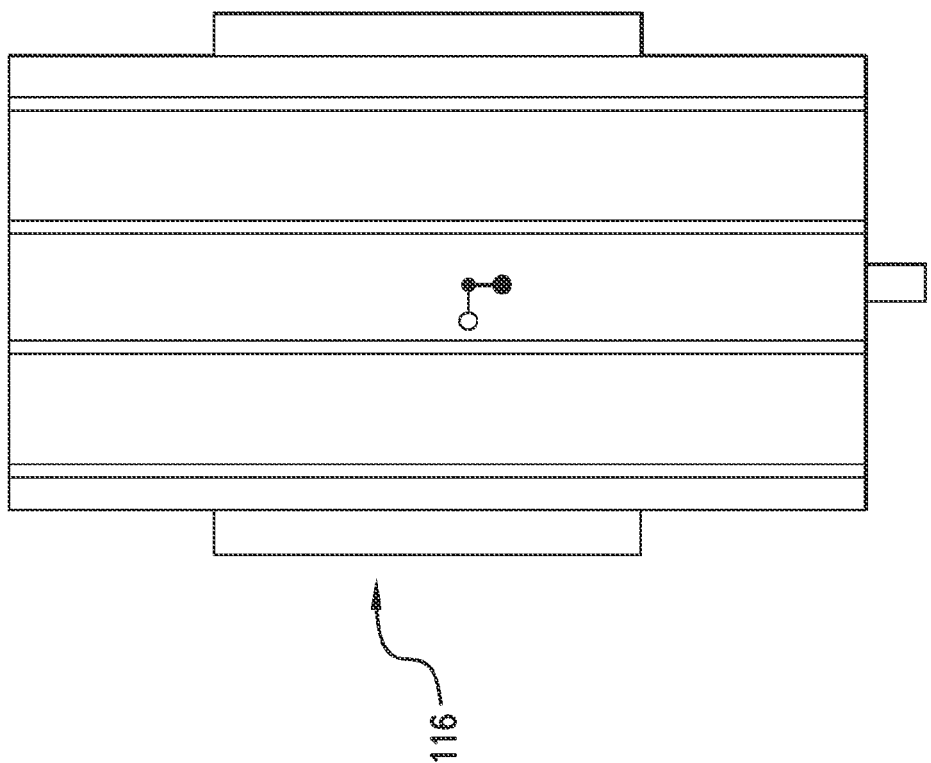
FIG. 6 is a front elevational view of a mounting member of a surgical machining system, according to another aspect of the present invention.

An exemplary mounting member 116 is illustrated in FIG. 6. In one aspect, the mounting member is substantially planar and defines slots that extend vertically therein. For example and as shown in FIG. 6, the mounting member can define four T-shaped slots. In one exemplary non-limiting aspect, the slots can be approximately 6 mm wide and spaced from each other (at their centers) at approximately 50 mm. In operation, the interfacing plate 124 can be mounted to the mounting member such that the interfacing plate (and attached surgical arm) can be moved up and down along the Z-axis, as described above. For example, and not meant to be limiting, at least one fastener can be used to fasten the interfacing plate, via a hole in the interfacing plate, to a corresponding slot in the mounting member. In a further exemplary aspect, a plurality of fasteners can be used to fasten the interfacing plate to the mounting member. For example, a fastener can be positioned within each of the holes of the interfacing plate 124. A corresponding head portion of each of the fasteners can be positioned within one of the T-shaped slots of the mounting member, thereby fastening the interfacing plate to the mounting member 116.

According to further aspects, the integrated surgical system 100 can comprise at least one imaging device such as, without limitation, a computed tomography (CT) device, a magnetic resonance imaging (MRI) device, an ultrasound device, and the like. The imaging device can be operably connected to the computing device 130 to transmit images to the processor 132 of the computing device.

In one aspect, the surgical machining system can comprise a contact cutting tool such as, for example and without limitation, a bio-compatible end-mill, and the like. In one exemplary aspect, the machining tool 120 can be a ¼ inch flat end mill with four flutes, one inch cutting length and four inches of overall length. In other aspects, the tool type can be a 3/16 inch end mill or a ⅜ inch end mill. However, it is contemplated that other tools can be selected based on rigidity, diameter, length of cut, avoiding excessive overhang of the tool from the holder and number of flutes. As known in the arts, diamond coated end mills can be used as they are biocompatible and are very commonly used as surgical end mills. In another aspect, the surgical machining system can comprise a non-contact tool such as a laser. Of course it is contemplated that the surgical machining system can be operably coupled to any desired surgical tool for subsequent operation along the generated optimized machine tool path.

In one aspect, machining tool 120 may be any tool used in machining the desired portion of the patient by changing a property of the desired portion, such as, but not limited to, through removing material from the desired portion of the patient to machine a finished surface. Although only one machining tool 120 is illustrated, it should be understood that the integrated surgical system 100 may include and/or cooperate with any number of machining tools 120 to facilitate changing any number and/or type of properties at any desired region of the patient.

Methods are provided for using the integrated surgical system as described herein to automate at least a portion of neurosurgeries and/or other surgeries that involve machining through bone and/or anatomical tissues. In one aspect, the methods described herein can be utilized to machine through a targeted portion of the patient, such as, for example and without limitation, bone or tissue. In another aspect, the methods described herein can be utilized to machine through substantially spatially fixed and/or relatively stable bone or tissue. In still another aspect, it is contemplated that the methods described herein can be utilized to machine through at least a portion of potentially spatially non-fixed tissue. In this aspect, for example, if a surgeon desired to remove a portion of a tumor, the methods described herein could be used to remove a desired portion of the tumor while maintaining a desired space from the identified edges of the tumor.

According to various aspects and as described above, it is contemplated that the methods can be performed using a combination of the hardware components of the systems as described herein, as well as software or computer program product code executing on a processor of the integrated surgical system. For convenience and clarity, the methods described herein are described with respect to neurosurgeries involving machining into the temporal bone of a patient's skull. It is contemplated, however, that the methods described herein can be utilized with any surgery and are not intended to be limited to neurosurgeries.

An exemplary method begins by scanning the patient to obtain images of the area to be accessed by the surgical machining system during surgery. In one aspect, the patient's head can be scanned using a CT device. Optionally, the patient's head can be scanned using an MRI device. Other devices capable of generating images of the patient's skull can likewise be used. According a further aspect, it is contemplated that a series of two-dimensional images are produced by the scanning device, such as is known in typical CT or MRI scans.

Figure 7:
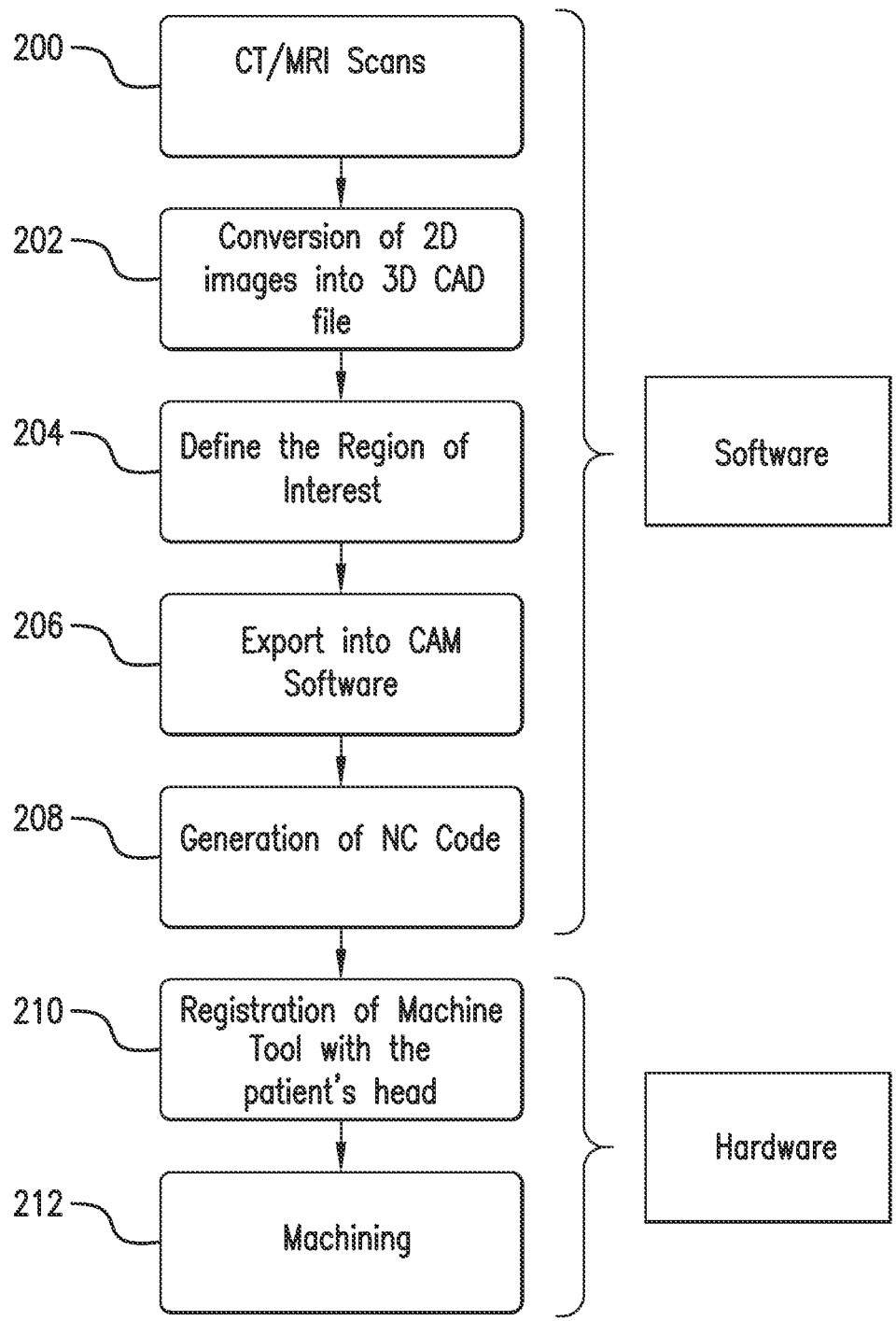
FIG. 7 is a flowchart illustrating a method for using an exemplary CNC system for neurosurgery according to another aspect of the present invention.
Figure 8:
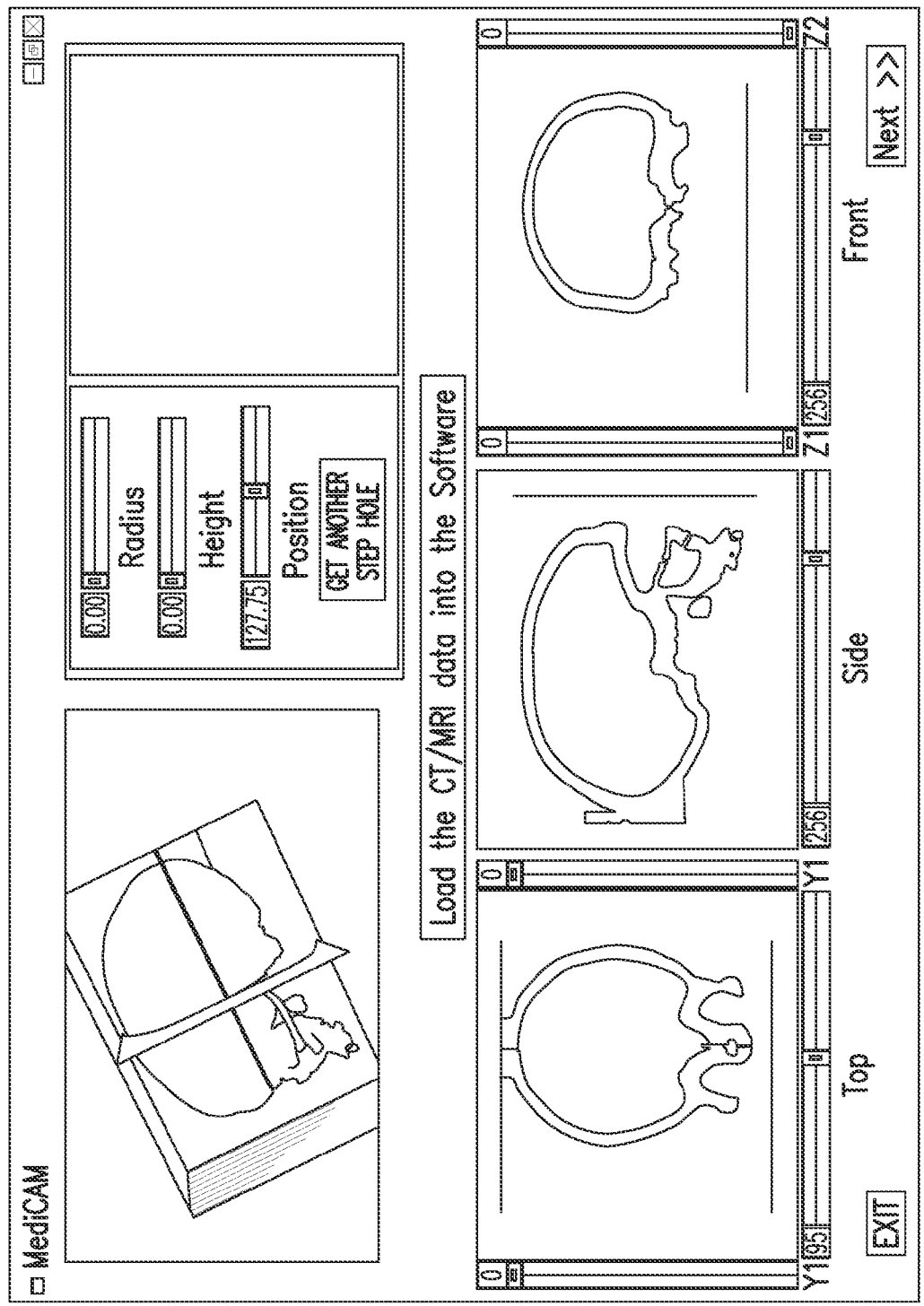
FIG. 8 is an exemplary screenshot illustrating CT/MRI data loaded into pre-operative planning software, according to one aspect of the present invention.
Figure 9:
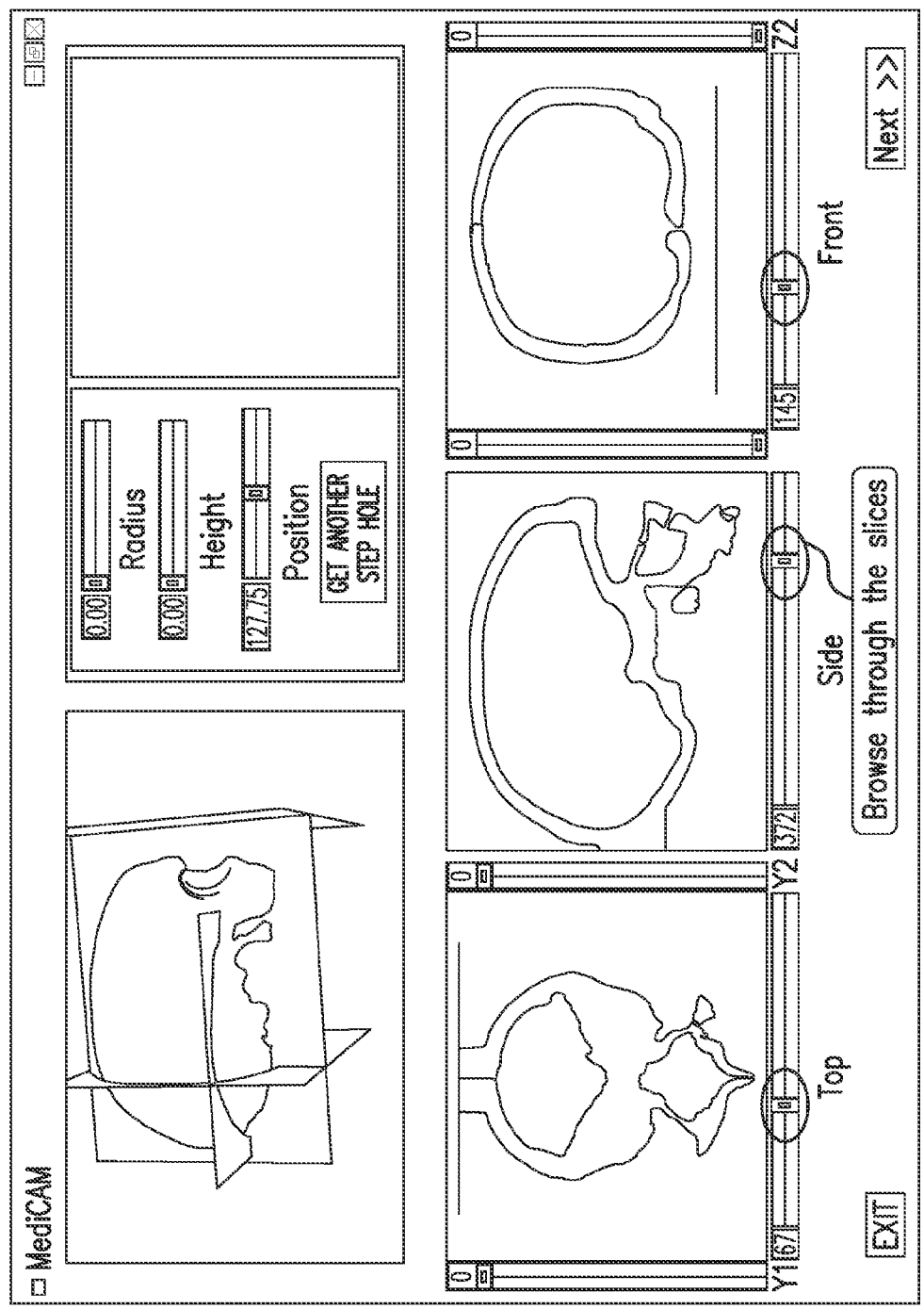
FIG. 9 is an exemplary screenshot of pre-operative planning software illustrating the function of browsing through slices of the CT/MRI data loaded into the software, according to yet another aspect of the present invention.
Figure 10:
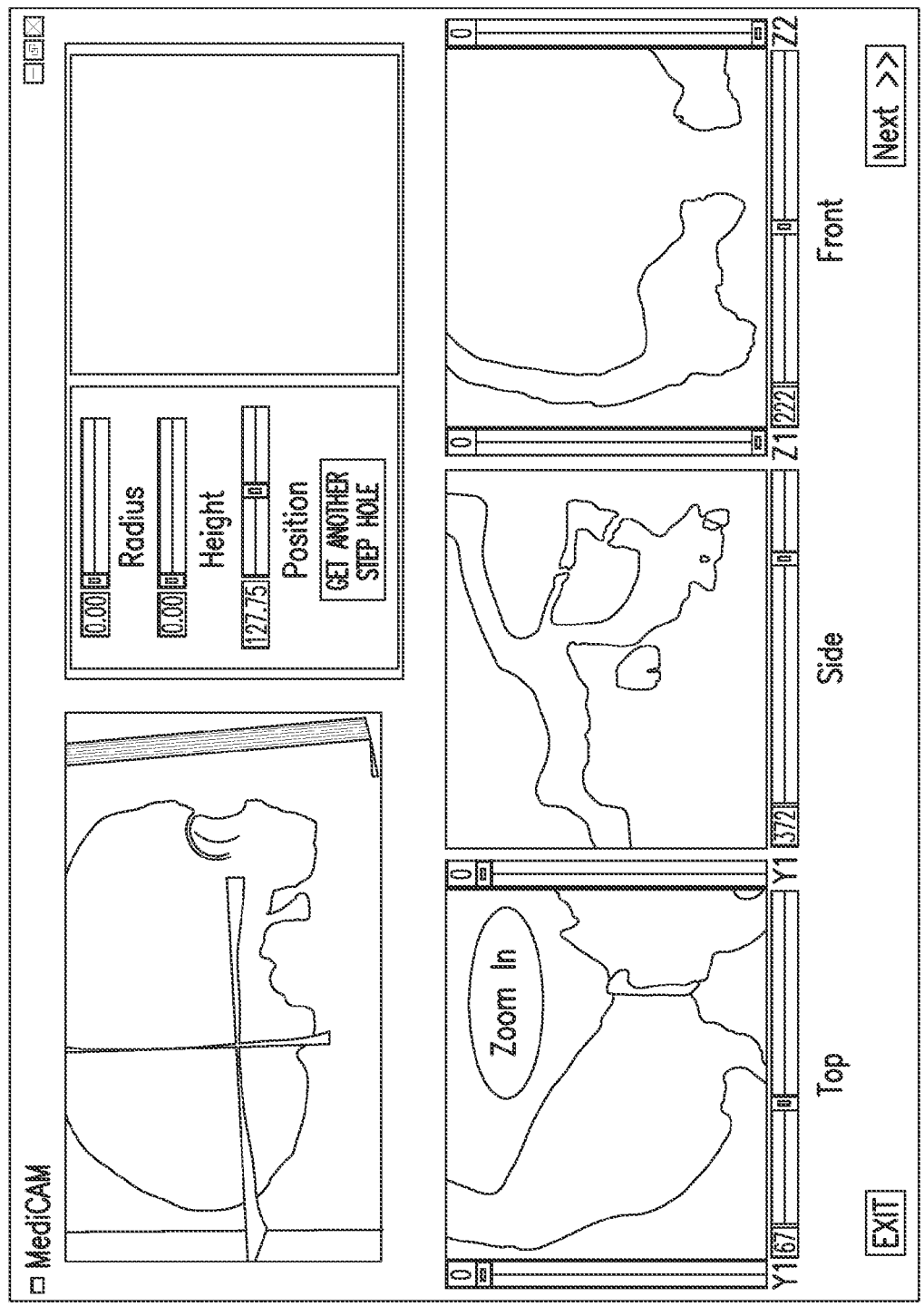
FIG. 10 is an exemplary screenshot of pre-operative planning software illustrating the function of zooming in to a slice of CT/MRI data loaded into the software, according to another aspect of the present invention.
Figure 11:
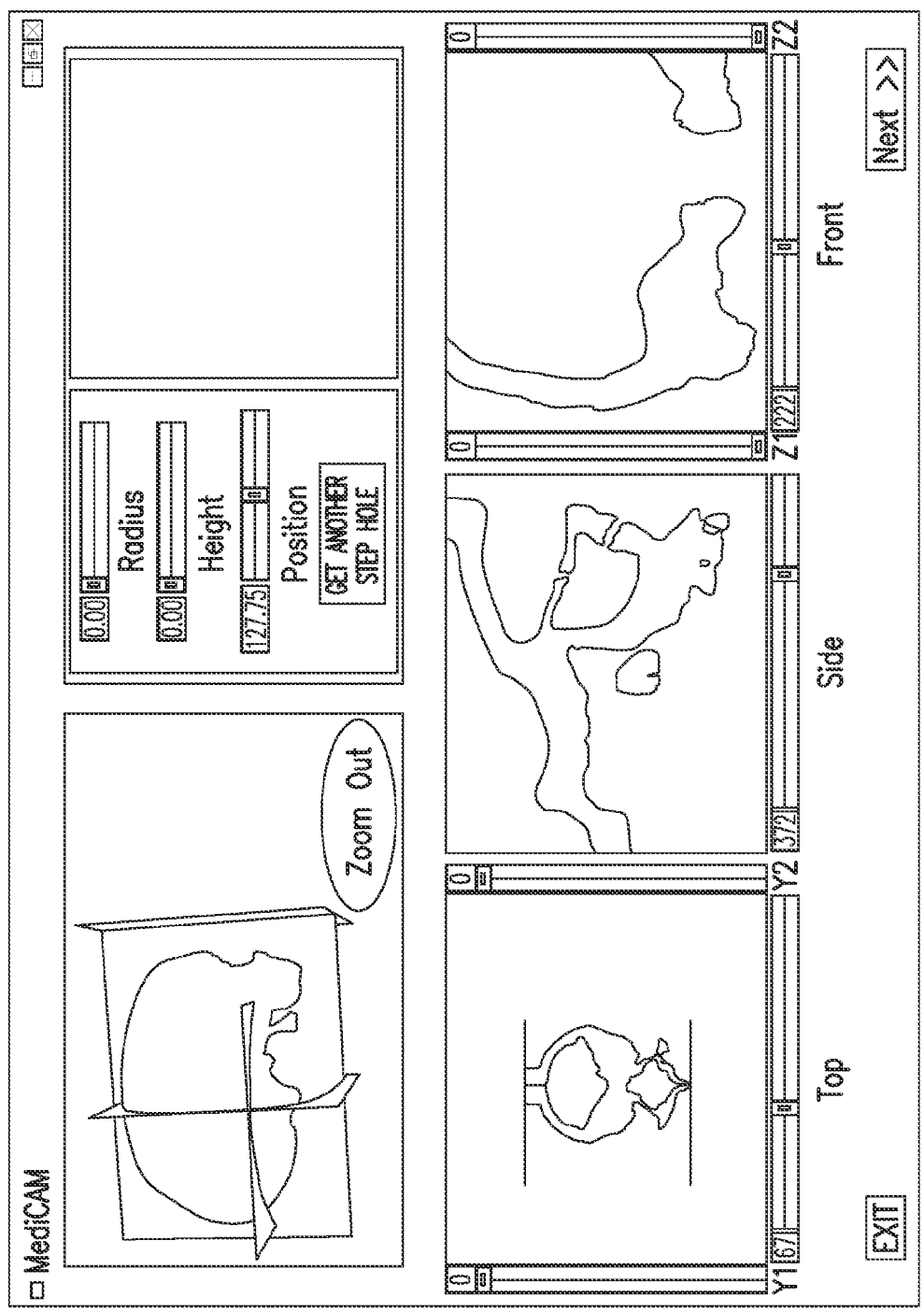
FIG. 11 is an exemplary screenshot of pre-operative planning software illustrating the function of zooming out of a slice of CT/MRI data loaded into the software, according to another aspect of the present invention.

As illustrated in FIG. 7, at step 200, the scanned images can be provided to the processor 132 of an exemplary integrated surgical system 100. At step 202, the scanned images are converted by the processor into a solid 3-dimensional model that can be accessed in CAD software. The 3D model, as well as at least one of the scanned images, can be displayed to a user via a monitor 134 or other display means of a computing device 130. FIG. 8 is a screenshot of exemplary software, showing the 3-dimensional model (upper left corner) formed from the scanned images, as well as "slices" or 2-dimensional images of the patient's skull. As can be seen, the slices show the skull from a top, side and front view. As shown in the screenshot of FIG. 9, the user of the software (such as, but not limited to, a physician, surgeon, or other medical professional) can browse through the slices to look at various portions of the patient's skull. Likewise, as shown in FIGS. 10 and 11 respectively, the user can zoom in or zoom out of the slices depending on the view that the user desires to have. As may be appreciated, the user can utilize various input/output devices such as described above to use the software.

Figure 12:
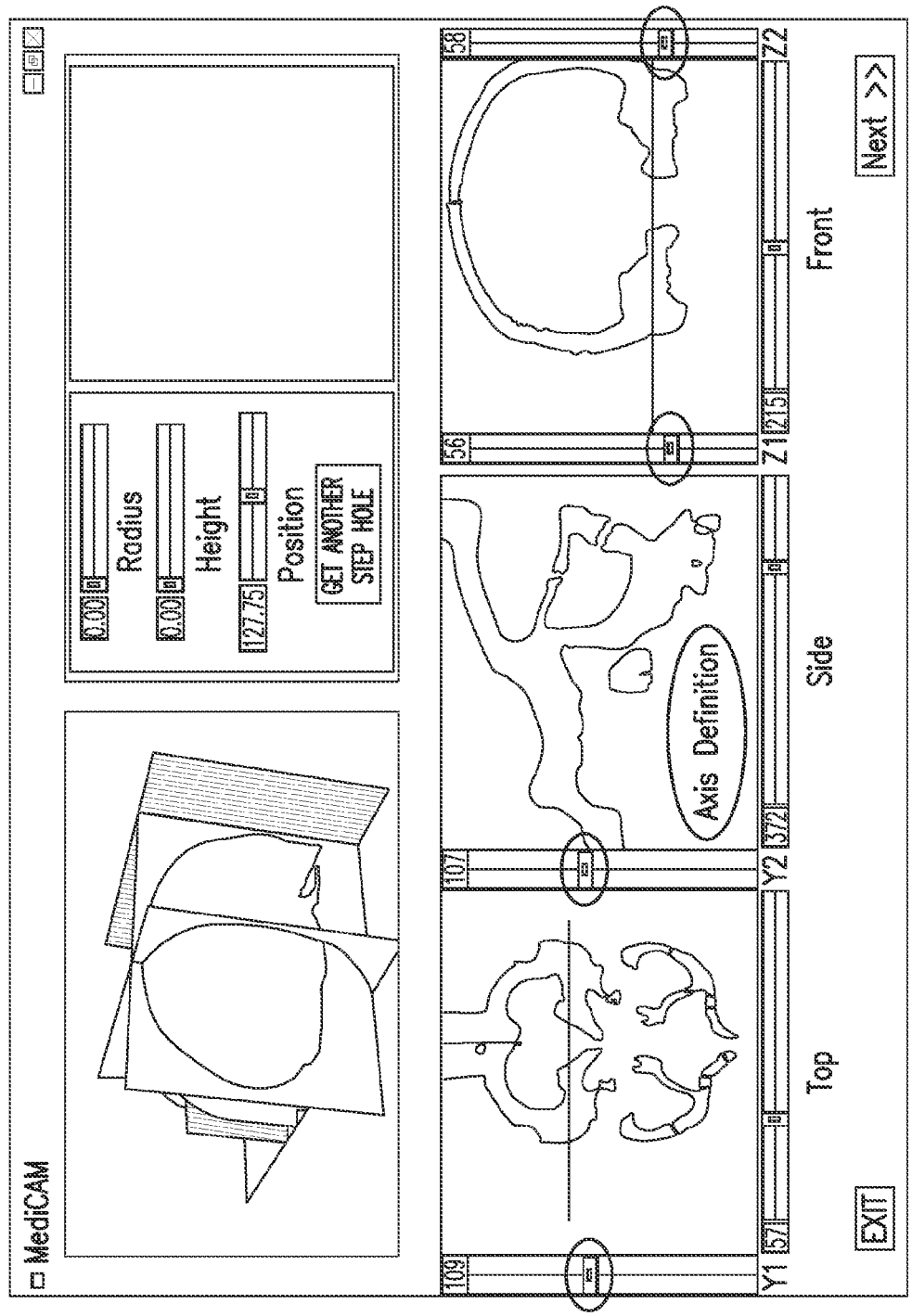
FIG. 12 is an exemplary screenshot of pre-operative planning software illustrating the function of axis definition, according to yet another aspect of the present invention.
Figure 13:
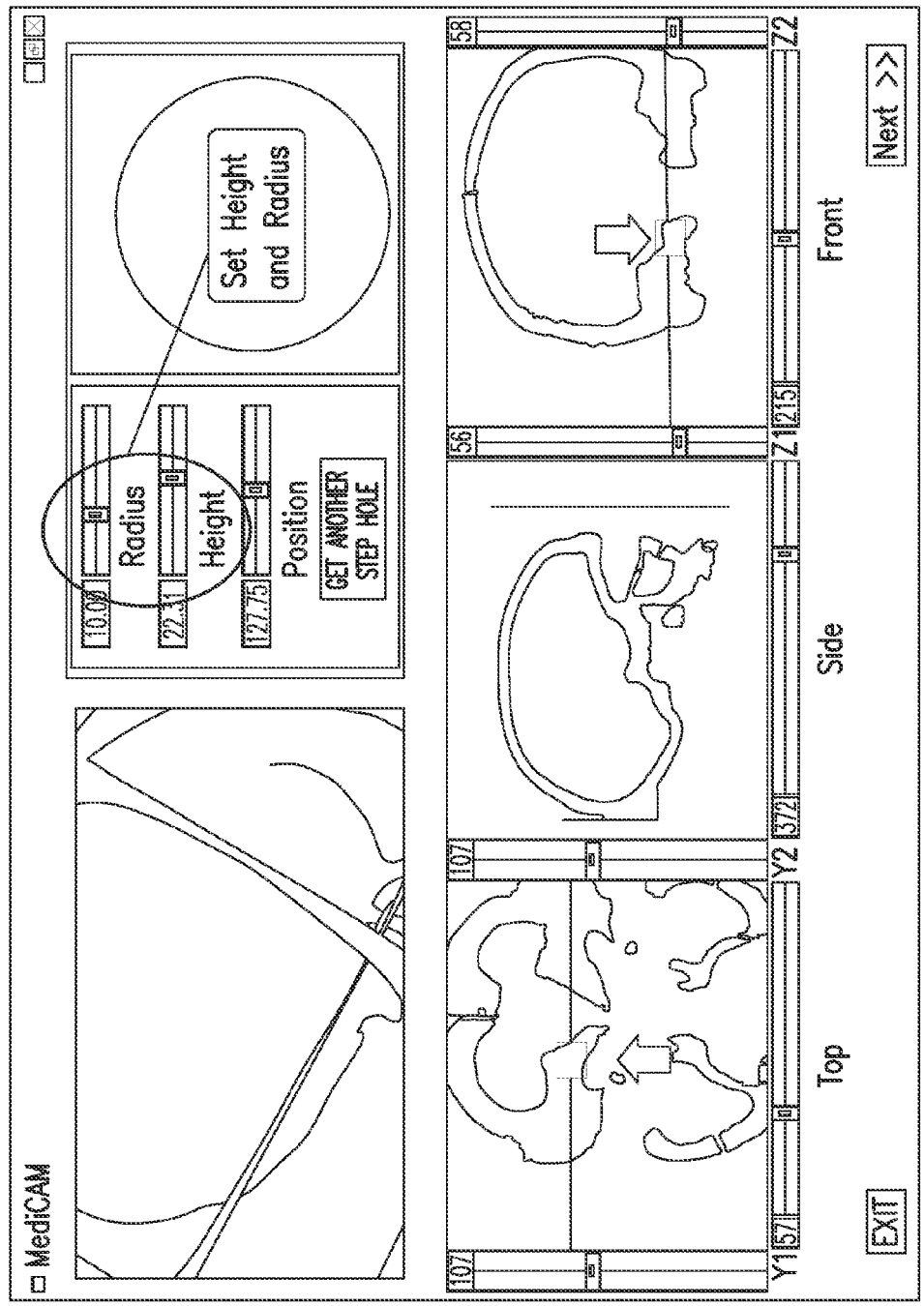
FIG. 13 is an exemplary screenshot of pre-operative planning software illustrating the function of dimensioning a hole to be machined, according to a further aspect of the present invention.
Figure 14:
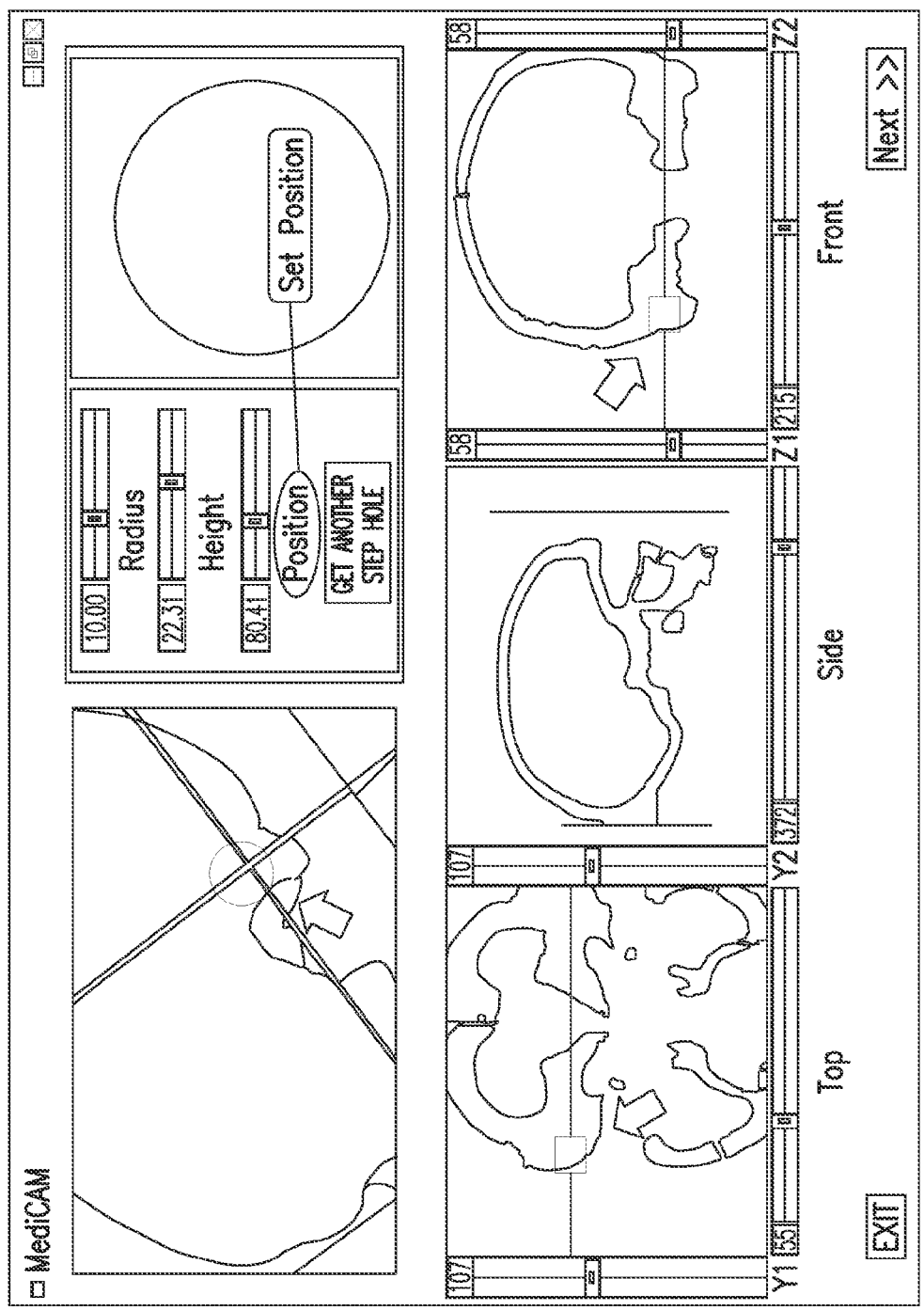
FIG. 14 is an exemplary screenshot of pre-operative planning software illustrating the function of positioning the hole to be machined of FIG. 13, according to another aspect of the present invention.
Figure 15:
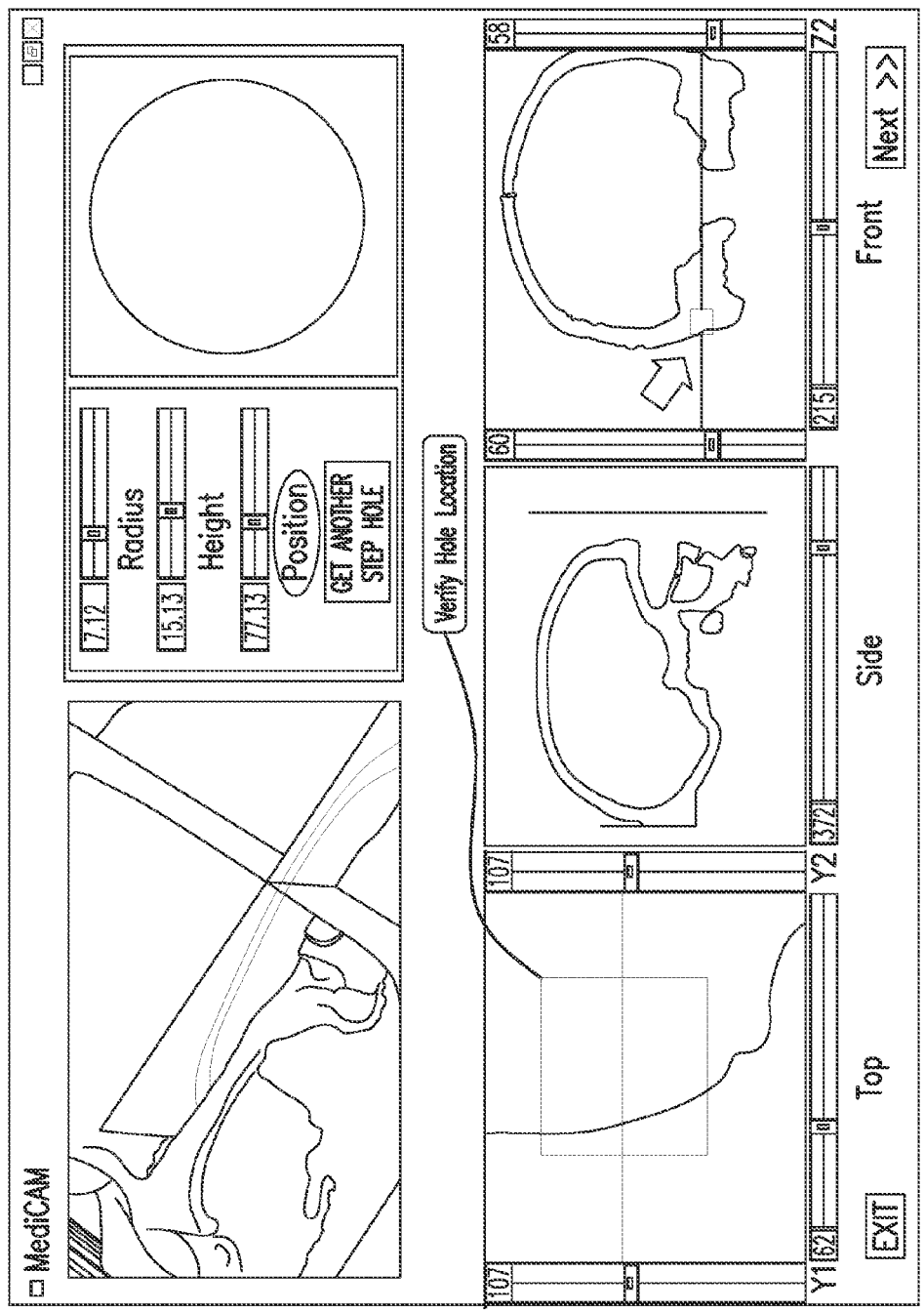
FIG. 15 is an exemplary screenshot of pre-operative planning software illustrating the function of verifying the position of the hole to be machined of FIG. 13, according to another aspect of the present invention.

At step 204, the user of the software can define the region of interest (i.e., the area of the skull to be machined). As shown in the screenshot of FIG. 12, the user can first define the axis along which the machining tool 120 is to machine. The user can then define the height and radius of the hole to be machined (FIG. 13). As shown in FIG. 14, the user can then set the position of the hole to be machined. As the user changes the parameters (such as the axis, height or depth of the hole, radius of the hole, etc.), the visual representations of the hole within the slices and the 3D model also change (as can be seen by comparing FIGS. 13 and 14). The user can then be presented with images showing the set position and size of the hole and can verify the hole parameters (FIG. 15).

Figure 16:
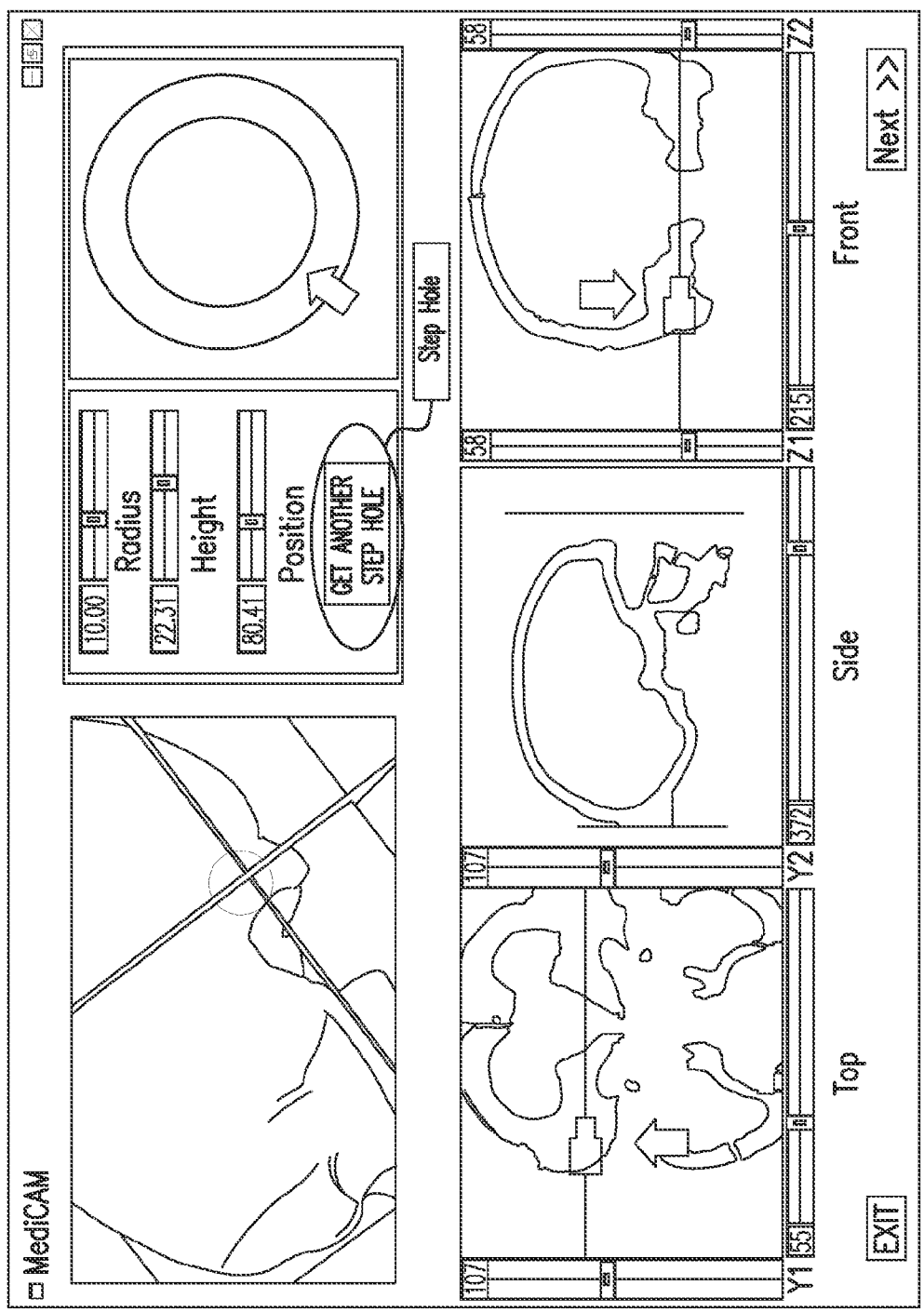
FIG. 16 is an exemplary screenshot of pre-operative planning software illustrating the function of defining a step hole extending from the machined hole of FIG. 13, according to a further aspect of the present invention.
Figure 17:
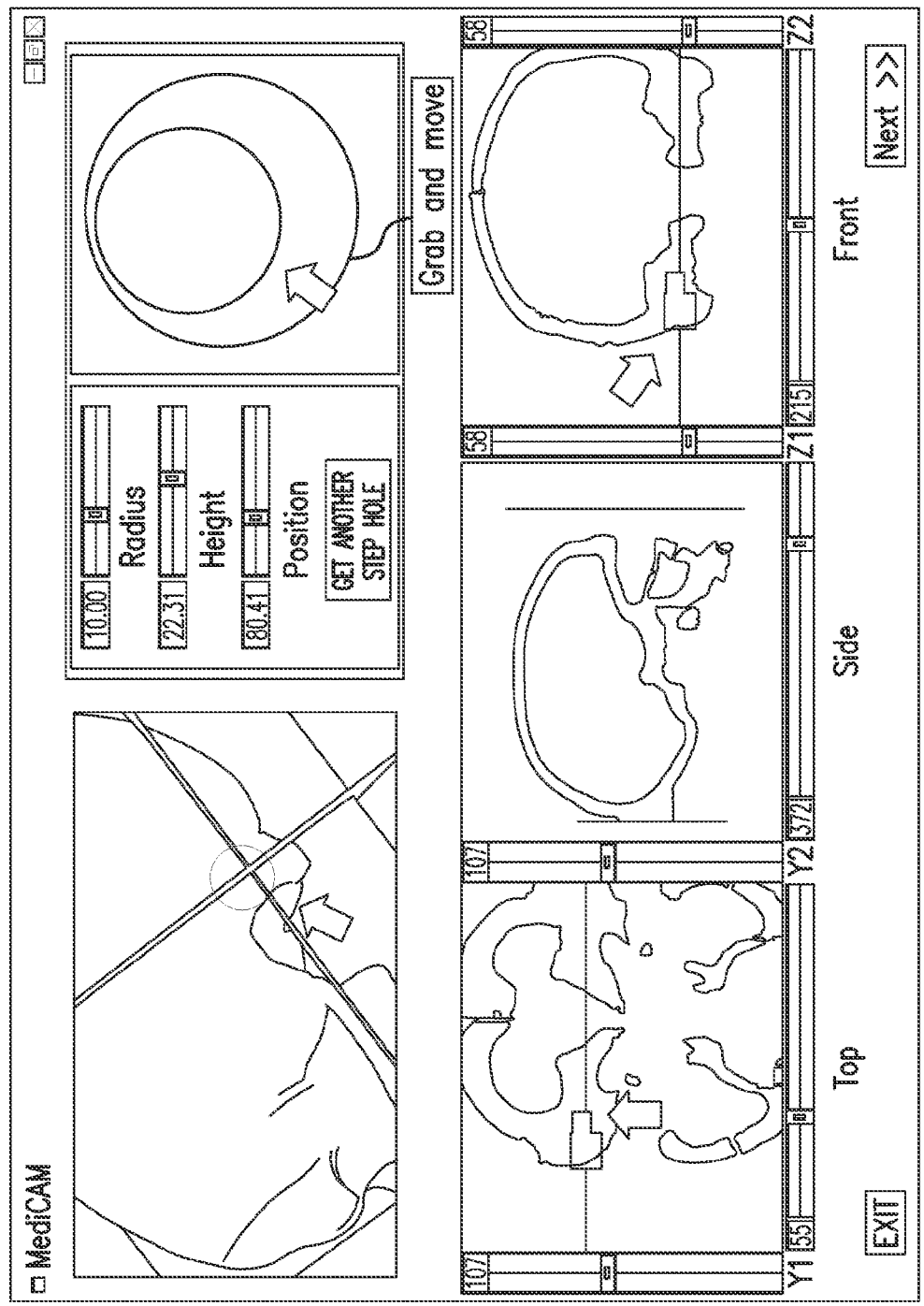
FIG. 17 is an exemplary screenshot of pre-operative planning software illustrating the function of positioning the step hole of FIG. 16, according to another aspect of the present invention.

In certain surgeries, it may be desirable to machine a step hole (such as, but not limited to, a hole that extends from the initial hole, but having a smaller diameter than the first hole). FIG. 16 is a screenshot showing the initial creation of a step hole, parameters of which can be set by the user (such as height and radius). As shown in FIG. 17, the position of the step hole relative to the initial hole can also be adjusted by the user. The above-described input of the user can then be exported into a CNC code module, at step 206. The CNC code module can assist in generating the numeric control code for the surgical machining system.

Figure 18:
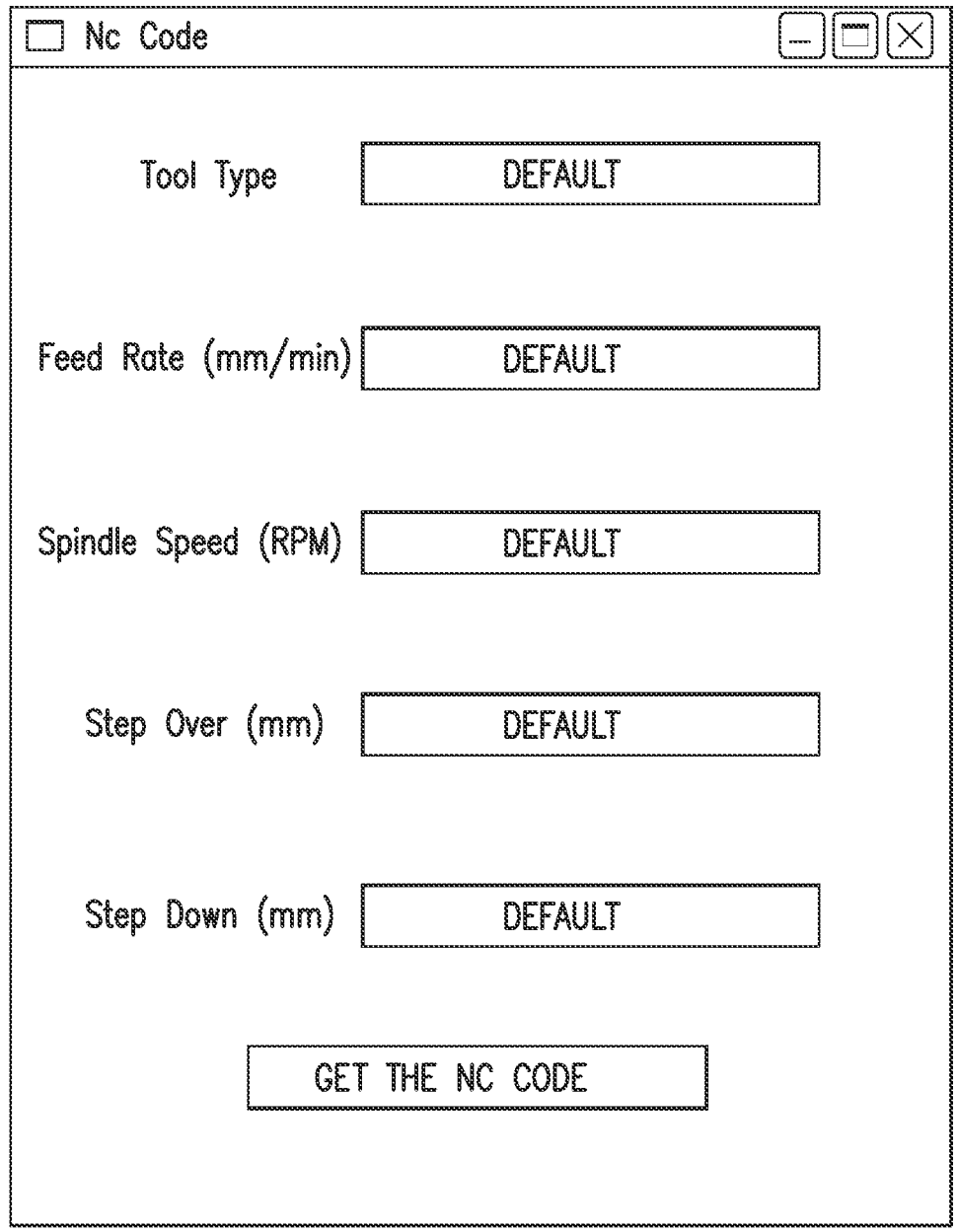
FIG. 18 is an exemplary screenshot of pre-operative planning software illustrating fields for entry of various information to generate CNC code, according to another aspect of the present invention.
Figure 21:
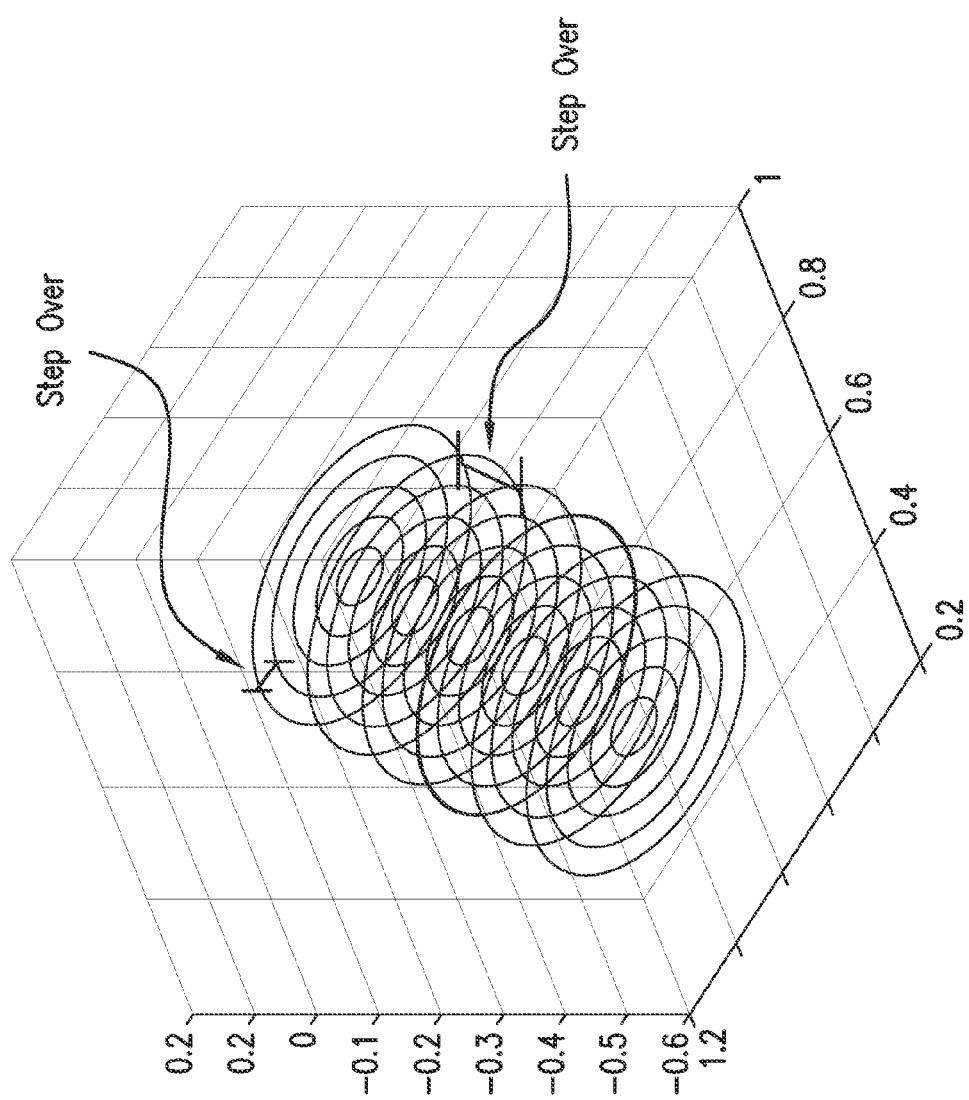
FIG. 21 is a graphical illustration of an exemplary tool path, according to one aspect of the present invention.

As illustrated in the screenshot of FIG. 18, prior to generating the numeric control code, the user can manually enter (or accept default settings) of additional parameters such as the tool type, feed rate, spindle speed, step over and step down. "Tool Type" allows a user to select the type of tool to be used in the machining. "Feed Rate" sets the rate at which X-axis and Y-axis motors move the components along these axes while the surgical machining system is in the process of cutting. Optionally, the feed rate can be between about 1.0 and 19.0 inches per minute ("ipm"), about 20.0 ipm, between about 21.0 and 31.0 ipm, about 31.2 ipm and greater than 31.2 ipm. "Spindle Speed" sets the revolutions per minute of the machining tool. Optionally, the spindle speed can be between about 1 and 8,000 rpm, about 8,000 rpm, between about 8,000 rpm and 24,000 rpm, and greater than 24,000 rpm. As shown in FIG. 21, "Step Over" sets the spacing between each horizontal coil of the pass and "Step Down" sets the spacing between each vertical coil of the pass. In one aspect, default values can be obtained from calibration of the system components or testing of the system components to determine optimal operating conditions.

The processor, at step 208, can then generate the numeric control code for the surgical machining system 110 and, more specifically, the machining tool 120. At step 210, the surgical machining system and machining tool are registered in relation to the patient's head. For example, the patient 150 can be positioned on the operating surface 152 or bed, as shown in FIG. 2A and can be fixed (i.e., restrained) in that position. To register the surgical machining system to the patient, it is contemplated that conventional surgical registration systems known in the art can be used. For example, it is contemplated that the patient can be registered to the surgical machining system 110 by using tactile position techniques which rely on touching fiduciaries placed on the patient, as commonly known in the arts. Once the desired portion of the patient 150 is fixed relative to the operating surface, the registration system can be used to identify the patient's orientation on the operating surface and define the patient's coordinate system. The surgical machining system can then be registered to the patient's coordinate system. In this exemplary aspect, the registration can be accomplished by moving the tip of the machining tool 120 (i.e., the point of first contact with the patient) to a plurality of different locations, for example and without limitation, three locations, and measuring the coordinates of these positions in the patient coordinate system using the registration system.

The machining tool can then be mapped to the patient's coordinate system using simple geometric transforms. The transforms will report the angle between the surgical machining system's Z-axis and the patient's respective Z-axis. The registration is then repeated to verify accurate adjustment of the angle of the machining tool tip. Thus, the registration procedure is repeated until all of the transformation values in the registration module are zero. Using the coordinates from the latter set of measurements, a three-axis ($\partial x$, $\partial y$, $\partial z$) offset is calculated between the surgical machining system coordinate system and the patient coordinate system. Finally, the pre-calculated tool path program is updated to account for this offset and a final motion plan is generated. At step 212, the surgical machining system 110 can begin machining a hole in the patient's skull (e.g., the temporal bone).

Figure 20:
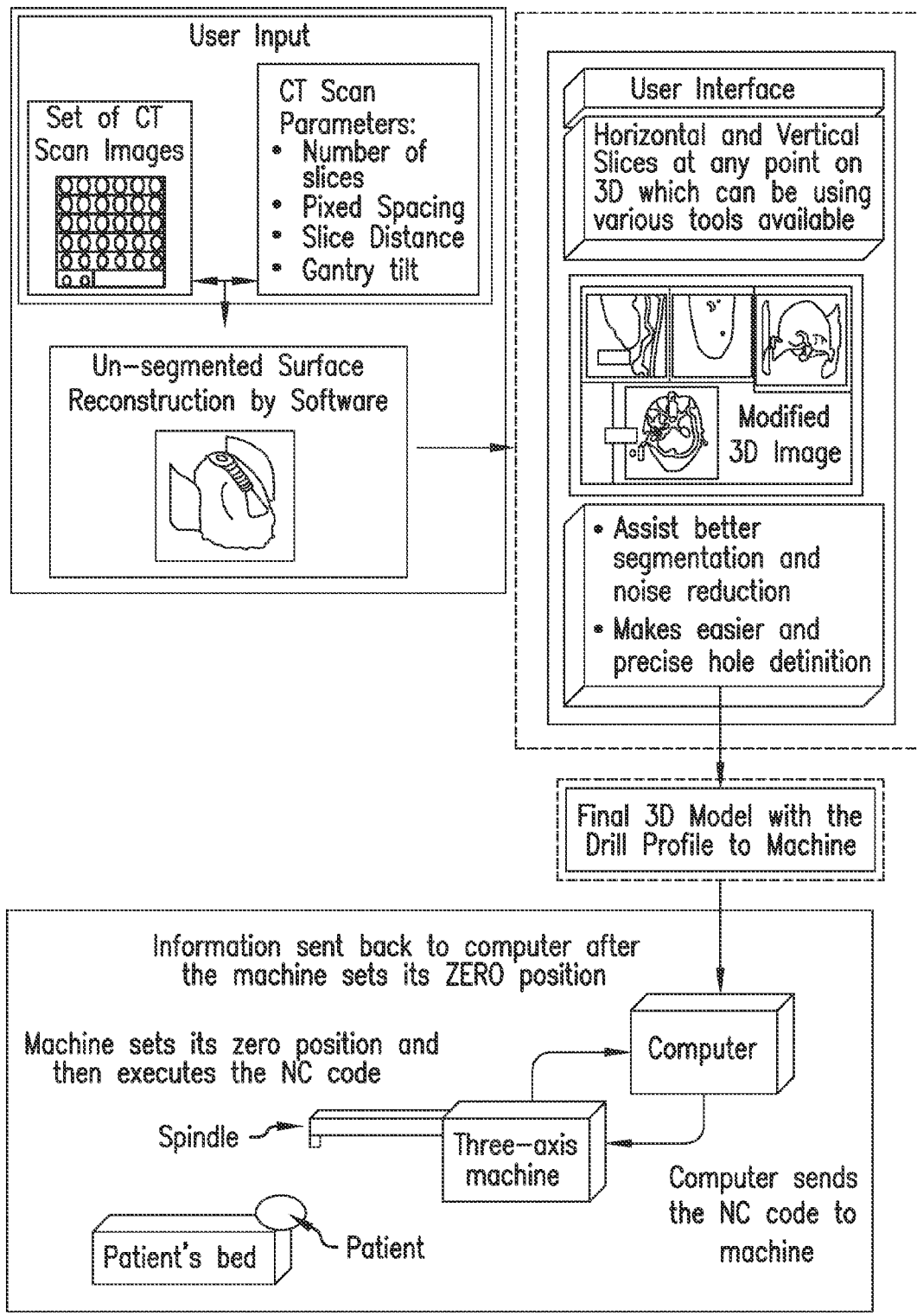
FIG. 20 is a schematic diagram of a method for using an exemplary CNC system for surgery according to another aspect of the present invention.

An exemplary method for using an exemplary CNC system for surgery according to another aspect of the present invention is illustrated schematically in FIG. 20. In one aspect, a user of the system can input a 2D image of a patient, such as, for example and without limitation, a CT scan. A 3D image can be constructed and 2D and/or 3D images can be displayed on a user interface. The user interface can allow the user to select "slices" of the patient for viewing, and the user can define the properties of the hole to be machined into the patient. The properties of the hole to be machined can be exported into a CNC code module that can assist in creating the numeric control code for the machining device. The numeric control code can be sent to the machining device, which can register the patient and execute the numeric control code.

In use, the surgical machining system 110 can machine the region of interest (the hole), as illustrated in FIG. 19, for example. In one aspect, the surgical machining system can machine the region of interest as input into the system by the surgical specialist or other user at step 204 within very close tolerances. In one aspect, the surgical machining system can machine the region of interest within a tolerance of +/−about 0.3200 mm. In another aspect, the surgical machining system can machine the region of interest within a tolerance of +/−about 0.0950 mm. In still another aspect, the surgical machining system can machine the region of interest within a tolerance of +/−about 0.0080 mm.

In another embodiment, the integrated surgical system 100 can further comprise an active imaging system interfaced with the passive imaging system described above. In one aspect, an active imaging system, as known in the arts, can be coupled to the computing device 130 and can be configured to transmit real-time images to the processor 132 of the computing device. Thus, it is contemplated that the surgical specialist can use the passive imaging system described above to preplan a tool path, and an active imaging system to monitor the machining process in real time. In another aspect, the integrated surgical system 100 can comprise a feedback loop using the active imaging system to provide real-time information about the position of the machine tool and/or the patient. In still another aspect, it is contemplated that the integrated surgical system can comprise a sensor or other detection means to notify the surgical specialist based upon information from the active imaging system that the desired portion of the patient being operating on has moved relative to the surgical machining system 110. In this aspect, the integrated surgical system can send a signal to the surgical specialist and/or the surgical machining system can turn off the machine tool.

In another embodiment, the size of the surgical machining system and/or the machining tool 120 can be varied for different applications. For example, in one aspect, at least a portion of the machining tool can be sized to fit into a patient's mouth for performing dental procedures. In other aspect, the size of the surgical machining system and/or the machining tool can be varied for orthopedic and/or spinal surgeries and the like. In still another aspect, the size of the surgical machining system 110 and/or the machining tool can be sized appropriately for veterinary applications.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for automating at least a portion of a surgery, comprising:
    scanning a selected portion of a patient's body to generate a plurality of two-dimensional images of the selected portion;
    transmitting the plurality of two-dimensional images to a processor, wherein the processor is operatively connected to a surgical machining system comprising a machine tool;
    using the processor to generate a three-dimensional image of the selected portion from the plurality of two-dimensional images;
    using the processor to display the three-dimensional image to a user;
    using the processor to receive input from the user, wherein the input indicates a location of the selected portion to be machined during surgery and at least one machining property;
    using the processor to generate an optimized tool path based at least in part on the input and at least in part on geometry of the three-dimensional image of the selected portion of the patient's body;
    using the processor to transmit the optimized tool path to the surgical machining system to effect movement of the machine tool in accordance with the optimized tool path in an automated manner; and
    using the processor to update the optimized tool path based on detected differences between actual properties of the selected portion of the patient's body and expected properties of the three-dimensional image of the selected portion.

2. The method of claim 1, further comprising machining the selected portion of the patient's body in accordance with the optimized tool path.

3. The method of claim 2, further comprising registering the machining tool to the selected portion of the patient's body, wherein the step of registering the machining tool takes place prior to the step of machining the selected portion of the patient's body.

4. The method of claim 1, wherein the step of using the processor to display the three-dimensional image to the user further comprises using the processor to display at least one of the plurality of two-dimensional images to a user.

5. The method of claim 1, wherein the surgical machining system comprises a variable high speed machine.

6. The method of claim 1, wherein the surgical machining system comprises an automated computer numerical controlled surgical machining system.

7. The method of claim 1, wherein the machining property comprises at least one of a shape, a size, and an orientation.

8. The method of claim 7, wherein the machining property is selected from the group consisting of a machining axis, a machine hole radius, and a machine hole depth.

9. The method of claim 1, wherein the step of scanning a selected portion of a patio body is performed using a scanning device.

10. The method of claim 9, herein the scanning device comprises a computed tomography (CT) device.

11. The method of claim 9, wherein the scanning device comprises a magnetic resonance imaging (MRI) device.

12. The method of claim 9, wherein the scanning device comprises an ultrasound device.

13. The method of claim 1, wherein the step of using the processor to transmit the optimized tool path to the surgical machining system to effect movement of the machine tool comprises moving the machine tool relative to a plurality of axes.

14. The method of claim 1, wherein the machine tool is selected from the group consisting of a contact cutting tool and a laser.

\* \* \* \* \*